United States Patent
Bandy et al.

(10) Patent No.: US 7,148,803 B2
(45) Date of Patent: Dec. 12, 2006

(54) RADIO FREQUENCY IDENTIFICATION (RFID) BASED SENSOR NETWORKS

(75) Inventors: William R. Bandy, Gambrills, MD (US); John P. Peeters, Chincoteague, VA (US)

(73) Assignees: Symbol Technologies, Inc., Holtsville, NY (US); Altivera, LLC., Potomac, MD (US)

( * ) Notice: Subject to any disclaimer, the term of this patent is extended or adjusted under 35 U.S.C. 154(b) by 19 days.

(21) Appl. No.: 10/761,362

(22) Filed: Jan. 22, 2004

(65) Prior Publication Data

US 2005/0088299 A1  Apr. 28, 2005

Related U.S. Application Data

(60) Provisional application No. 60/513,740, filed on Oct. 24, 2003.

(51) Int. Cl.
*G08B 1/08* (2006.01)

(52) U.S. Cl. .............. 340/539.16; 340/10.1; 340/505; 340/539.17; 340/539.22; 340/539.26; 340/870.11; 340/870.16

(58) Field of Classification Search .......... 340/539.16, 340/539.17, 539.22, 539.26, 505, 506, 572.1, 340/572.4, 10.1, 10.3, 10.4, 870.01, 870.11, 340/870.16, 870.3, 870.4
See application file for complete search history.

(56) References Cited

U.S. PATENT DOCUMENTS

| | | | |
|---|---|---|---|
| 5,640,002 A | 6/1997 | Ruppert et al. | |
| 5,850,187 A | 12/1998 | Carrender et al. | |
| 6,002,344 A | 12/1999 | Bandy et al. | |
| 6,031,454 A | 2/2000 | Lovejoy et al. | |
| 6,095,985 A | 8/2000 | Raymond et al. | |
| 6,134,548 A | 10/2000 | Gottsman et al. | |
| 6,437,692 B1 * | 8/2002 | Petite et al. | 340/870.01 |
| 6,486,780 B1 | 11/2002 | Garber et al. | |
| 6,501,435 B1 | 12/2002 | King et al. | |
| 6,661,339 B1 | 12/2003 | Muirhead | |
| 6,720,866 B1 | 4/2004 | Sorrells et al. | |
| 6,731,223 B1 * | 5/2004 | Partyka | 340/870.15 |
| 6,856,247 B1 * | 2/2005 | Wallace | 340/539.16 |
| 6,943,678 B1 | 9/2005 | Muirhead | |
| 2002/0019584 A1 * | 2/2002 | Schulze et al. | 600/300 |
| 2002/0078363 A1 | 6/2002 | Hill et al. | |

(Continued)

OTHER PUBLICATIONS

Rick Merritt; "From Sea to Shining Sea, War on terror prompts U.S. plans for a national sensor network, to give early warning of nuclear, chemical and biological threats"; Electronic Engineering Times, Jul. 14, 2003; pp. 18, 19 and 24.

(Continued)

*Primary Examiner*—Thomas Mullen
(74) *Attorney, Agent, or Firm*—Sterne, Kessler, Goldstein & Fox

(57) ABSTRACT

An RF addressable sensor network architecture is provided. The RF addressable sensor network includes one or more RF addressable sensors, one or more wireless sensor readers coupled to a communications network, and one or more end user devices coupled to the communications network. The RF addressable sensor network may also include a sensor network processor. An RF addressable sensor includes one or more sensor elements, one or more antennas for communicating with the wireless sensor reader, an RF power and communications interface, an RFID control module, and a sensor interface. The wireless sensor reader includes one or more antennas, a user interface, a controller, a network communications module, and an RF addressable sensor logic module.

85 Claims, 16 Drawing Sheets

U.S. PATENT DOCUMENTS

| | | |
|---|---|---|
| 2002/0149481 A1 | 10/2002 | Shanks et al. |
| 2002/0149483 A1 | 10/2002 | Shanks et al. |
| 2002/0167405 A1 | 11/2002 | Shanks et al. |
| 2002/0170961 A1 | 11/2002 | Dickson et al. |
| 2002/0170969 A1 | 11/2002 | Bridgelall |
| 2003/0085267 A1 | 5/2003 | Piotrowski et al. |
| 2003/0106931 A1 | 6/2003 | Wu et al. |
| 2003/0109905 A1 | 6/2003 | Mok et al. |
| 2003/0114986 A1 | 6/2003 | Padmanabhan et al. |
| 2003/0120745 A1 | 6/2003 | Katagishi et al. |
| 2003/0128119 A1 | 7/2003 | Lake et al. |
| 2003/0146783 A1 | 8/2003 | Bandy et al. |
| 2003/0167207 A1 | 9/2003 | Berardi et al. |
| 2003/0174046 A1 | 9/2003 | Abrams |
| 2004/0008114 A1 | 1/2004 | Sawyer |
| 2004/0100394 A1* | 5/2004 | Hitt ........................ 340/870.11 |
| 2004/0113790 A1* | 6/2004 | Hamel et al. ............. 340/572.1 |
| 2004/0119591 A1 | 6/2004 | Peeters |
| 2004/0134984 A1 | 7/2004 | Powell et al. |
| 2004/0135674 A1 | 7/2004 | Shanks et al. |
| 2004/0168618 A1 | 9/2004 | Muirhead |
| 2004/0212500 A1* | 10/2004 | Stilp ........................ 340/572.1 |
| 2005/0087235 A1* | 4/2005 | Skorpik et al. ............. 137/554 |
| 2005/0237184 A1 | 10/2005 | Muirhead |

OTHER PUBLICATIONS

Roy Want; "RFID A Key to Automating Everything:" Scientific American, Jan., 2004; pp. 56, 57, 58, 59, 60, 61, 62, 63, 64 and 65.

(AP); "Bar codes matching drug to patient coming soon;" CNN.com, Health, Dec. 9, 2003; pp. 1,2 and 3.

RFID Enables "Physical Browsing;" RFID Journal, May 6, 2003; pp. 1-2.

Bandy et al, U.S. Appl. No. 09/323,206, filed Jun. 1, 1999, entitled "System and Method for Electronic Inventory".

Arneson et al., U.S. Appl. No. 09/496,960, filed Feb. 3, 2000, Arneson et al, entitled "Automated Real-Time Distributed Tag Reader Network".

"*Nokia Unveils RFID Phone Reader*", RFID Journal, URL http://www.rfidjournal.com/article/articleprint/834/-1/1/, Mar. 17, 2004, 2 pages.

International Search Report in PCT Application No. PCT/US04/35149 dated Mar. 28, 2006.

* cited by examiner

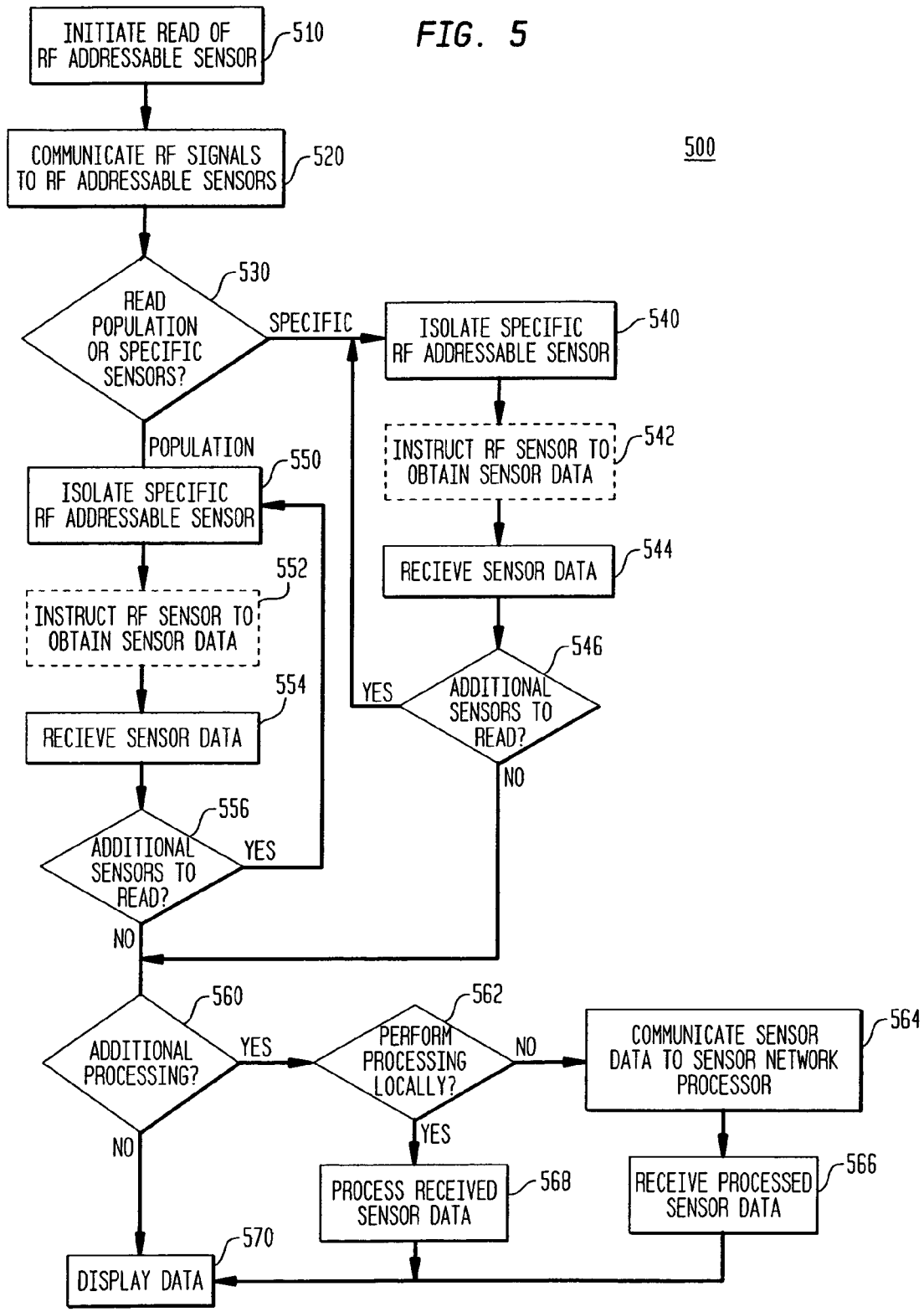

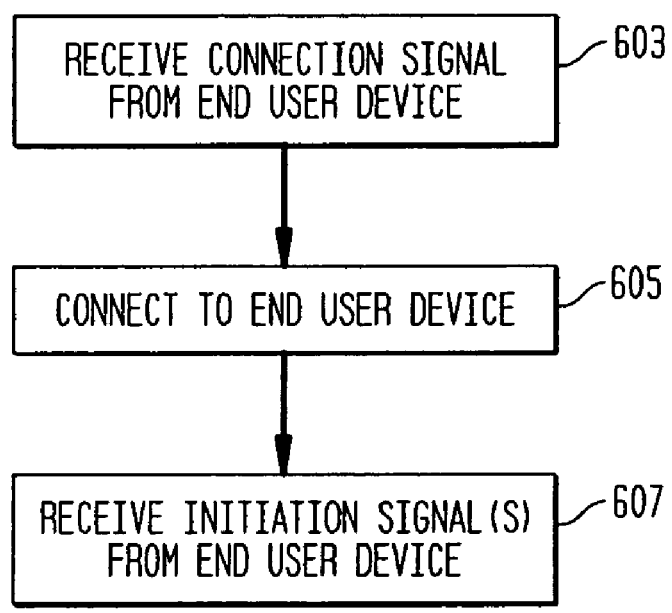

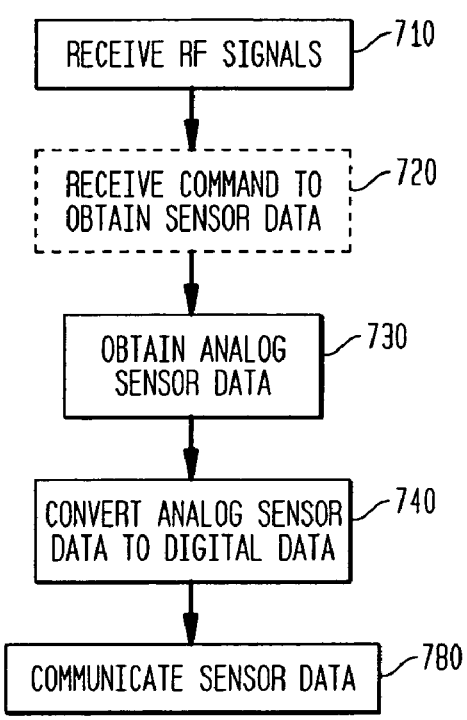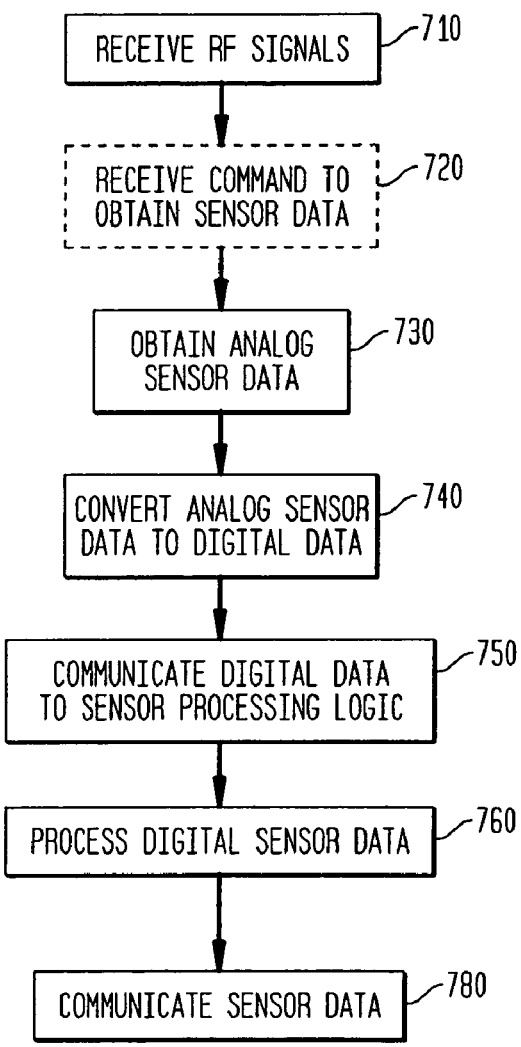

RADIO FREQUENCY IDENTIFICATION (RFID) BASED SENSOR NETWORKS

CROSS REFERENCE TO RELATED APPLICATIONS

This application claims priority to U.S. Provisional Application No. 60/513,740, entitled "Low Cost Distributed Chemical RFID Sensor Networks," filed Oct. 24, 2003, which is incorporated herein by reference in its entirety.

FIELD OF THE INVENTION

The present invention relates generally to sensor networks and specifically to radio frequency identification (RFID) based sensor networks.

BACKGROUND OF THE INVENTION

The ability of wireless sensors to remotely provide data in real-time opens up a wide variety of health and safety applications. From the perspective of an individual, the ability to determine, prior to consumption, whether a food item contains harmful bacteria or ingredients to which the individual is allergic is highly desirable. From a community perspective, recent national and international events have increased the need for distributed systems for the continuous, real-time monitoring and detection of chemical agents, biological agents, radiological agents, and other hazards over wide geographical areas.

Because of the cost of sensors and sensor readers, broad deployment of a sensor network over a large geographical area or widespread use by individuals is currently not feasible. In addition, the imprecision of sensors generally requires cross validation to eliminate false positives, adding to the number of sensors that must be deployed for each application. Another problem with large geographical deployment is that the wear of sensors or sensor surfaces requires sensors to be replaced on a regular basis, adding to the cost.

Hence, what is needed is a wireless sensor that is inexpensive, small, and flexible. Furthermore, what is needed is a sensor reader that is inexpensive and accessible to the general population.

The need also exists for distributed sensor networks for the real time monitoring and detection of hazardous materials and/or conditions in a highly cost effective way.

BRIEF SUMMARY OF THE INVENTION

The present invention is directed to a radio frequency (RF) addressable sensor network architecture where a reader communicates with and powers RF addressable sensors. The present invention is also directed to RF addressable sensors that may be produced at costs lower than most types of sensors that are currently available.

In accordance with aspects of the present invention, the RF addressable sensor network includes one or more RF addressable sensors, one or more wireless sensor readers coupled to a communications network, and one or more optional end user devices coupled to the communications network. In an aspect of the present invention, the communications network is a publicly accessible communications network. In another aspect, the communications network is a private network or is a hybrid network having both public and private portions. The wireless sensor readers communicate with the RF addressable sensors via RF signals. The wireless sensor readers also communicate with the communications network via a wireless air interface protocol or via a wired data communications protocol. In another aspect of the invention, the RF addressable sensor network includes a sensor network processor having sensor data processing logic and geolocation processing logic.

The RF addressable sensor combines radio frequency identification (RFID) tag functionality and sensor functionality. The RF addressable sensor includes one or more antennas for communicating with the wireless sensor reader, one or more sensor elements, an RF power and communications interface, an RFID control module, and a sensor interface. The RFID control module includes RFID logic to control RFID tag communications with the wireless sensor reader and/or a conventional RFID tag reader. The RFID control module may also include logic to process sensor data. In another aspect of the invention, the RF addressable sensor includes one or more reference elements coupled in parallel with the sensor elements.

The present invention is also directed to a wireless sensor reader. According to aspects of the present invention, the wireless sensor reader includes one or more antennas, a user interface, a controller, a network communications module, and an RF addressable sensor logic module. The network communications module is configured to provide communication with a communications network. The RF addressable sensor logic module controls communication with the RF addressable sensors. The wireless sensor reader is implemented in a wireless device such as a phone or PDA. In an aspect of the invention, the RF addressable sensor logic module is integrated into the device either by design or by downloading the sensor logic into a programmable processor located on the device. In another aspect of the invention, RF addressable sensor logic module is coupled to the device via an interface.

The present invention is also directed to a method for communicating sensor data in a RFID based sensor network. In accordance with an aspect of the present invention, a read of one or more RF addressable sensors is initiated at the wireless sensor reader. The wireless sensor reader then communicates signals to the RF addressable sensors to initialize and power the sensors. The wireless sensor reader then isolates an individual RF addressable sensor. In an aspect of the present invention, the wireless sensor reader signals the isolated RF addressable sensor to obtain sensor data. The RF addressable sensor then communicates the sensor data to the wireless sensor reader. The wireless sensor reader may perform additional processing on the data or may communicate the data to the network sensor processor for additional processing. In some aspects of the present invention, the received sensor data and/or processed sensor data can be displayed on the wireless sensor reader. In another aspect of the present invention, the original sensor data and/or the processed sensor data are communicated to a processor and/or end-user device coupled to the communications network.

These and other objects, advantages and features will become readily apparent in view of the following detailed description of the invention.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

Figure 4A:
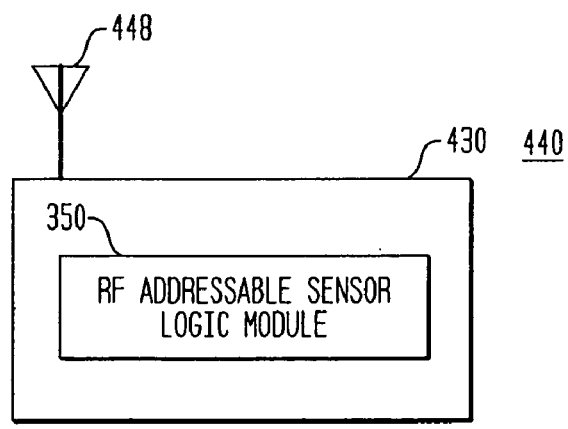
Figure 4B:
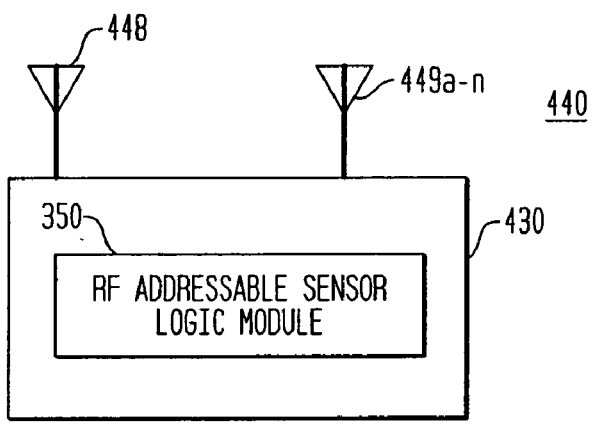
Figure 4C:
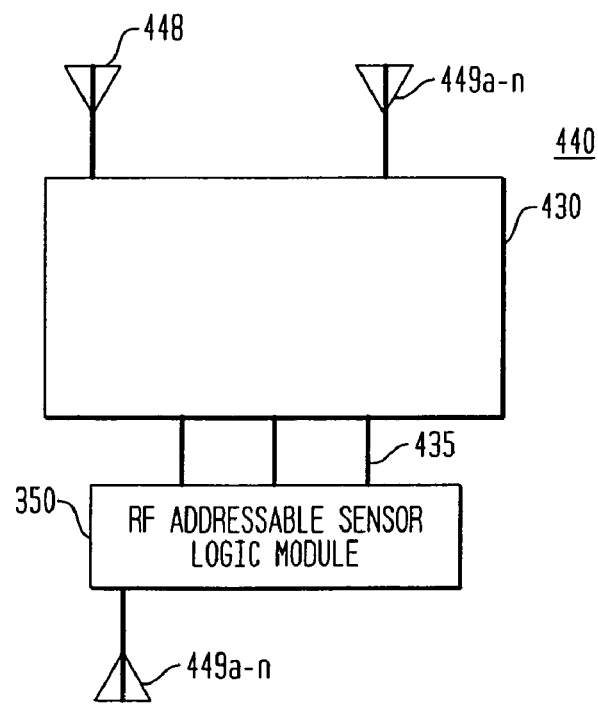

FIGS. 4A, 4B, and 4C are block diagrams of illustrative wireless sensor reader configurations according to embodiments of the present invention.

FIG. 5 is a flowchart illustrating an operational sequence of RF addressable sensor read communications from the perspective of the wireless sensor reader according to an embodiment of the present invention.

FIG. 6 is a flowchart illustrating a method for remotely initiating a sensor read over a communications network according to an embodiment of the present invention.

FIG. 7A is a flowchart illustrating a method of RF addressable sensor read communications from the perspective of a basic single RF addressable sensor according to an embodiment of the present invention.

FIG. 7B is a flowchart illustrating a method of RF addressable sensor read communications from the perspective of an RF addressable sensor having local processing capabilities according to an embodiment of the present invention.

Figure 8:
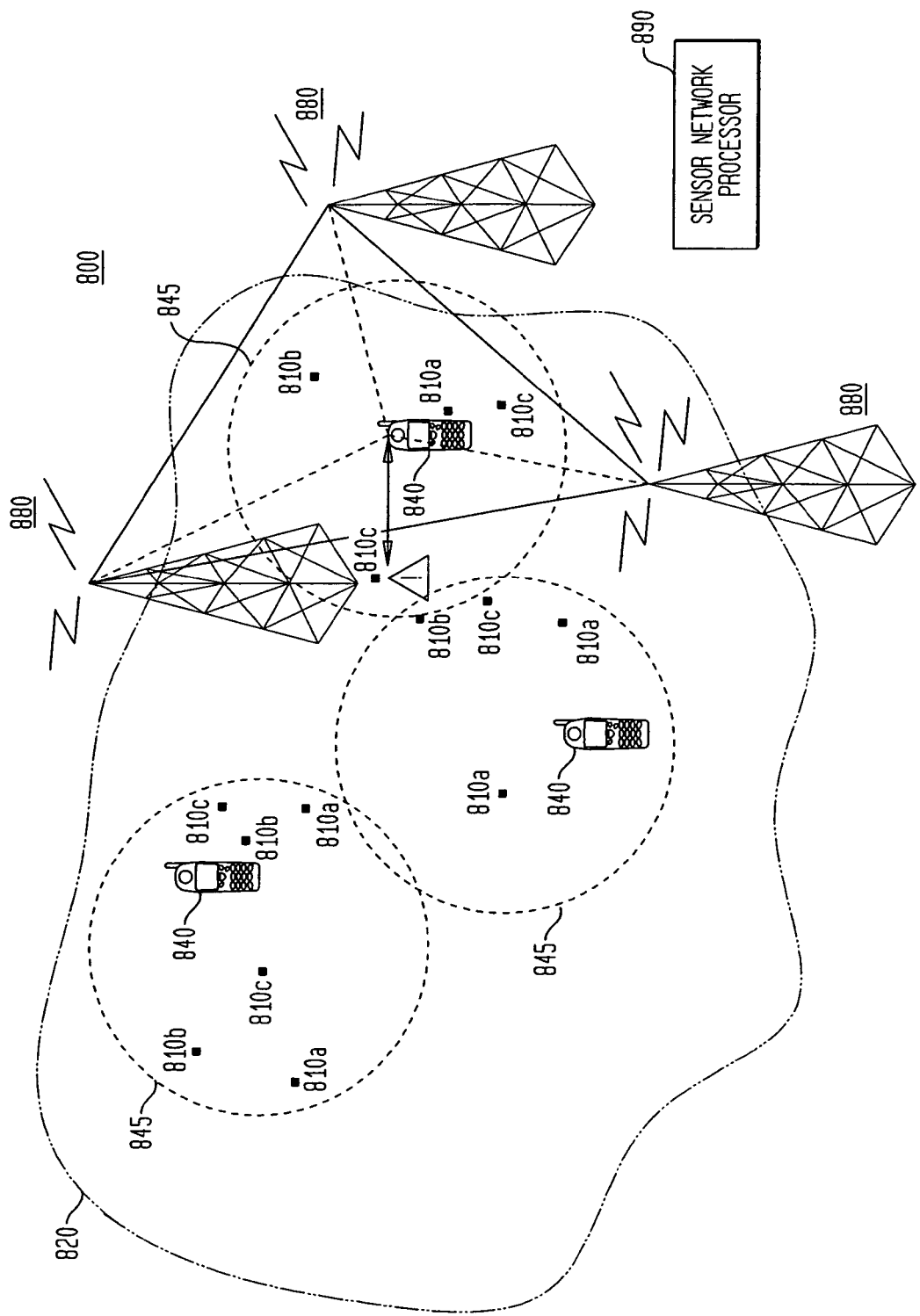

FIG. 8 depicts a block diagram of a homeland security sensor network application having geolocation capabilities, according to an example embodiment of the present invention.

Figure 9:
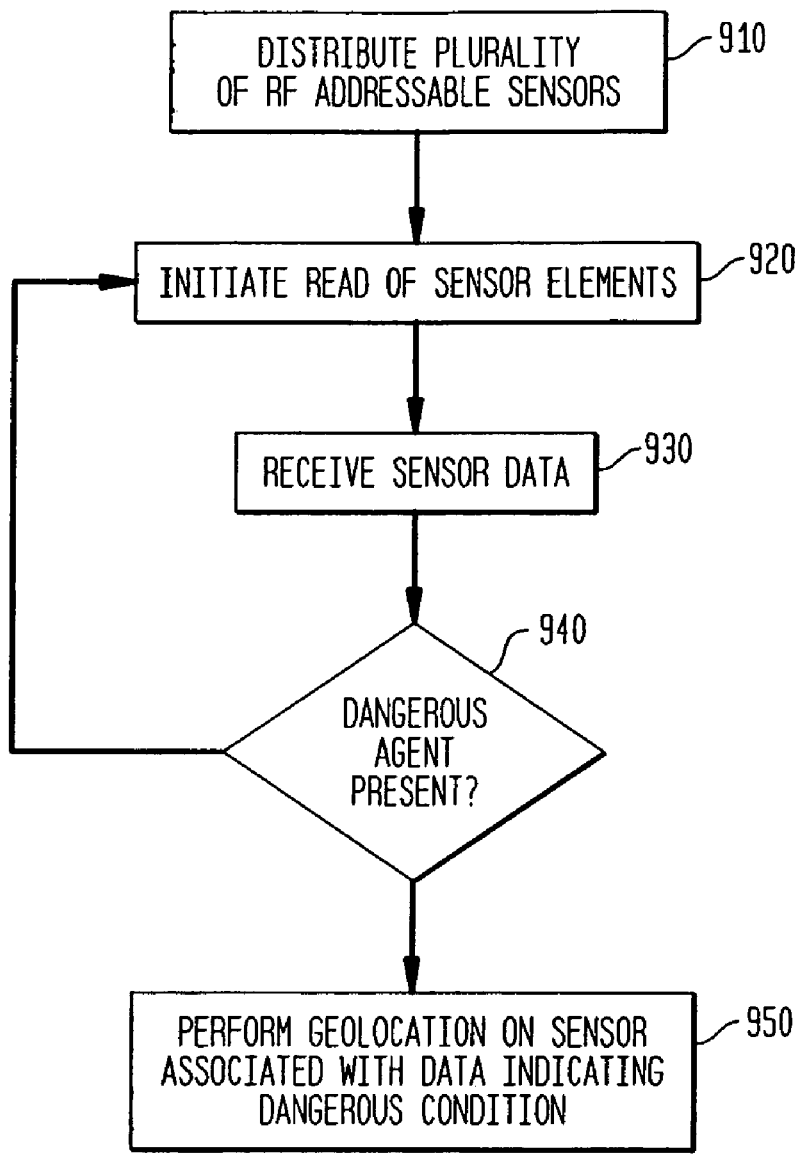

FIG. 9 is a flowchart illustrating a method of sensing the presence of dangerous agents in a homeland security sensor network, according to an example embodiment of the present invention.

Figure 10:
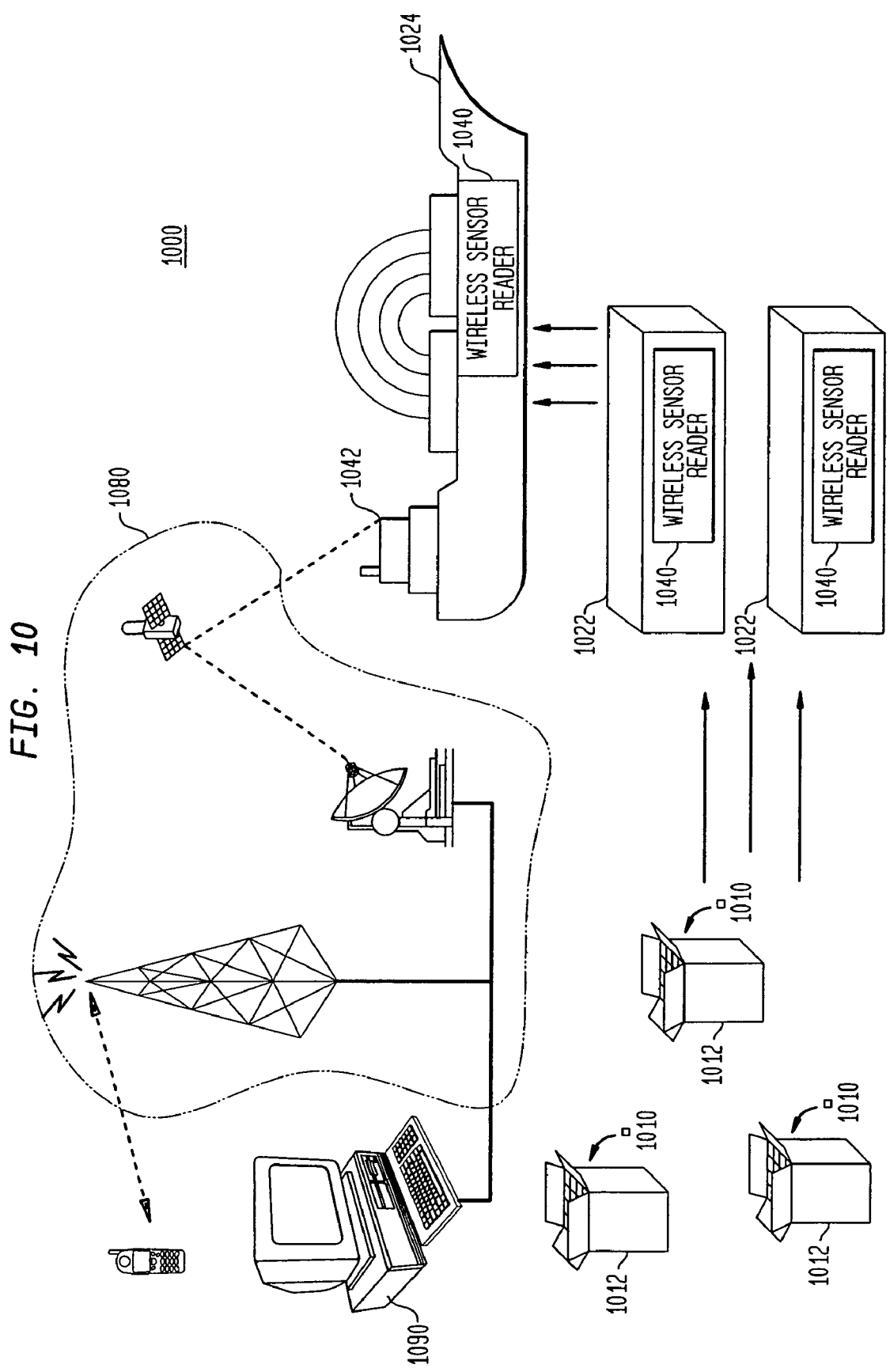

FIG. 10 depicts a block diagram of an application of a sensor network for the remote monitoring of shipping containers, according to an example embodiment of the present invention.

Figure 11:
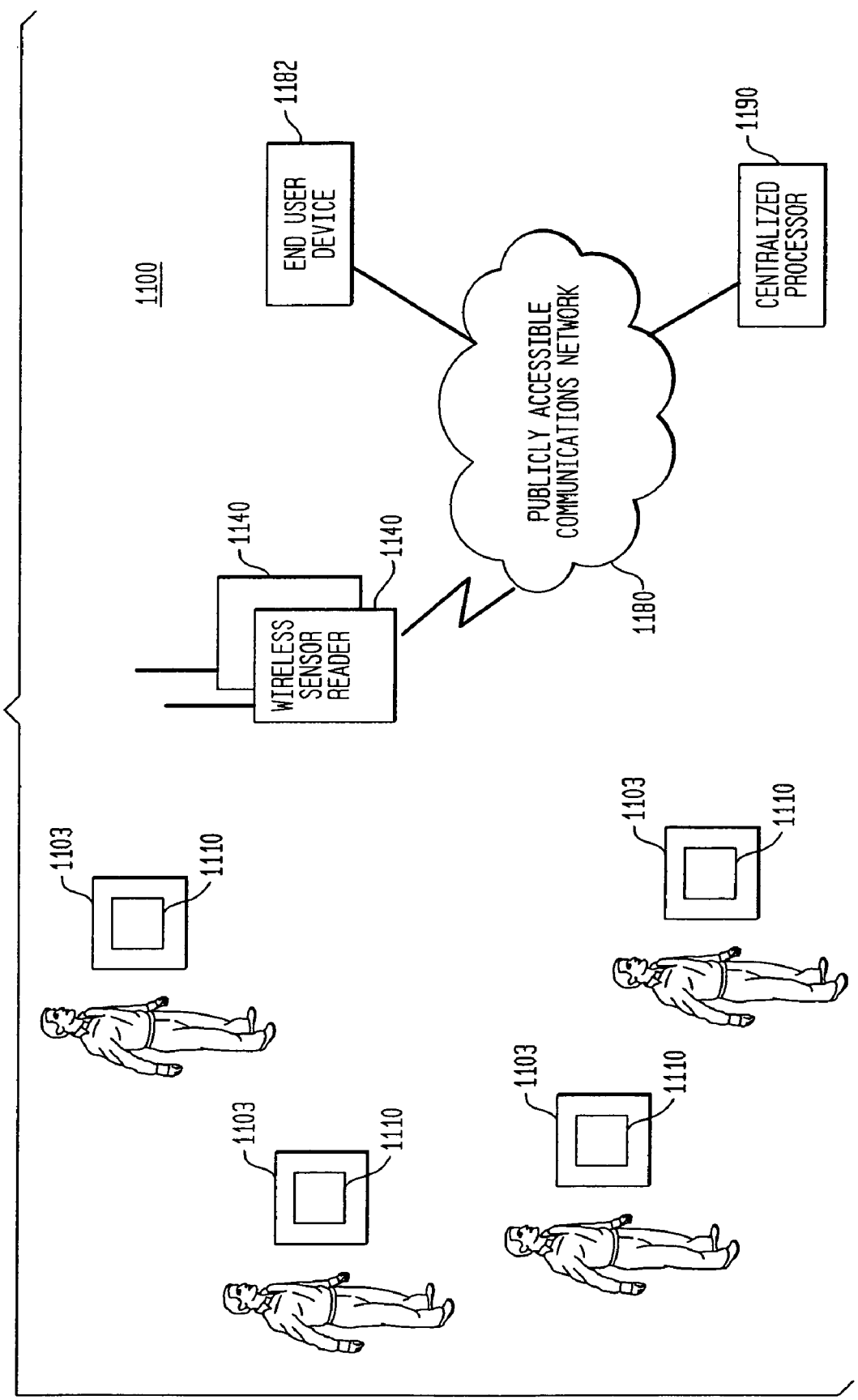

FIG. 11 depicts a block diagram of an application of a sensor network for remote monitoring smart cards or badges having one or more RF addressable sensors, according to an example embodiment of the present invention.

Figure 12:
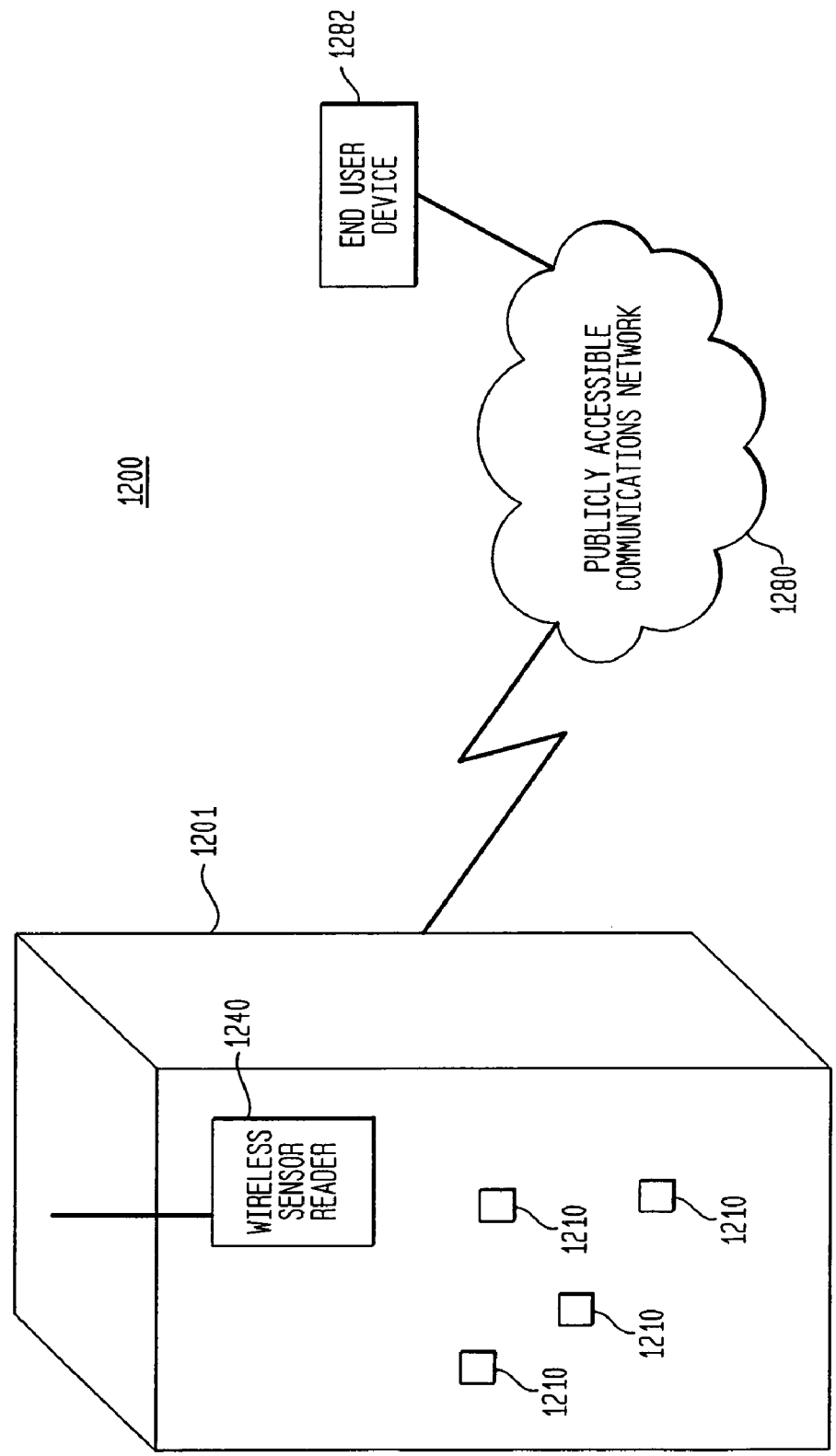

FIG. 12 depicts a block diagram of an application of a sensor network for remote monitoring of the contents of a network appliance, according to an example embodiment of the present invention.

Figure 13A:
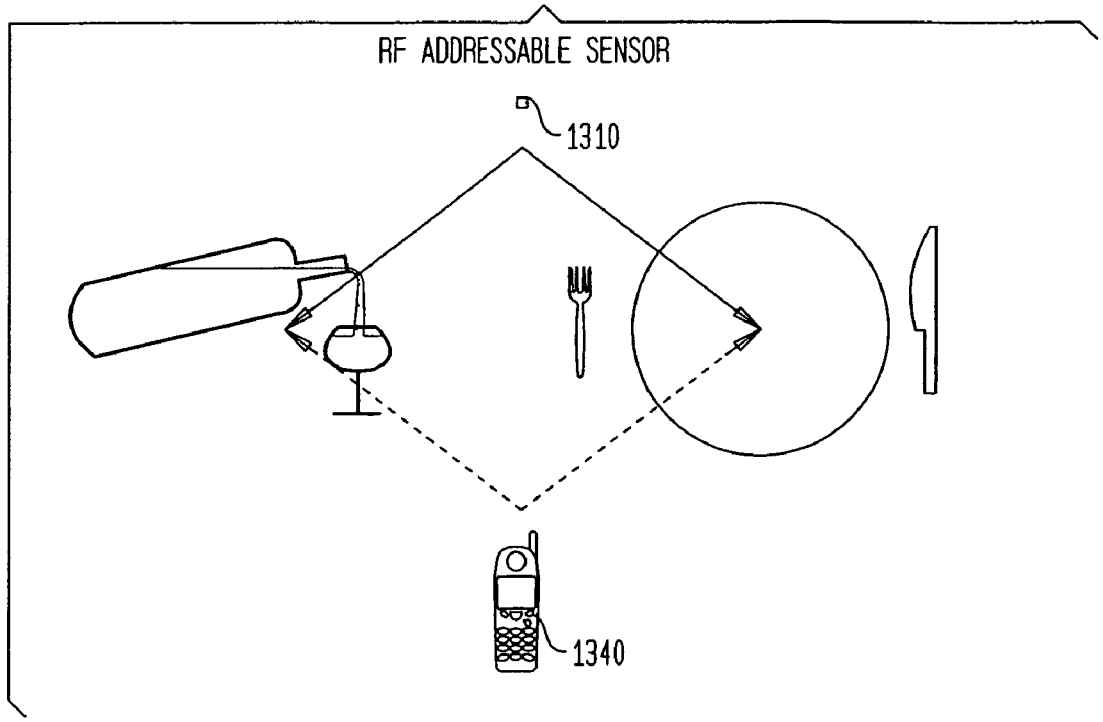

FIG. 13A depicts a block diagram of an example real-time food testing application, according to an example embodiment of the present invention.

Figure 13B:
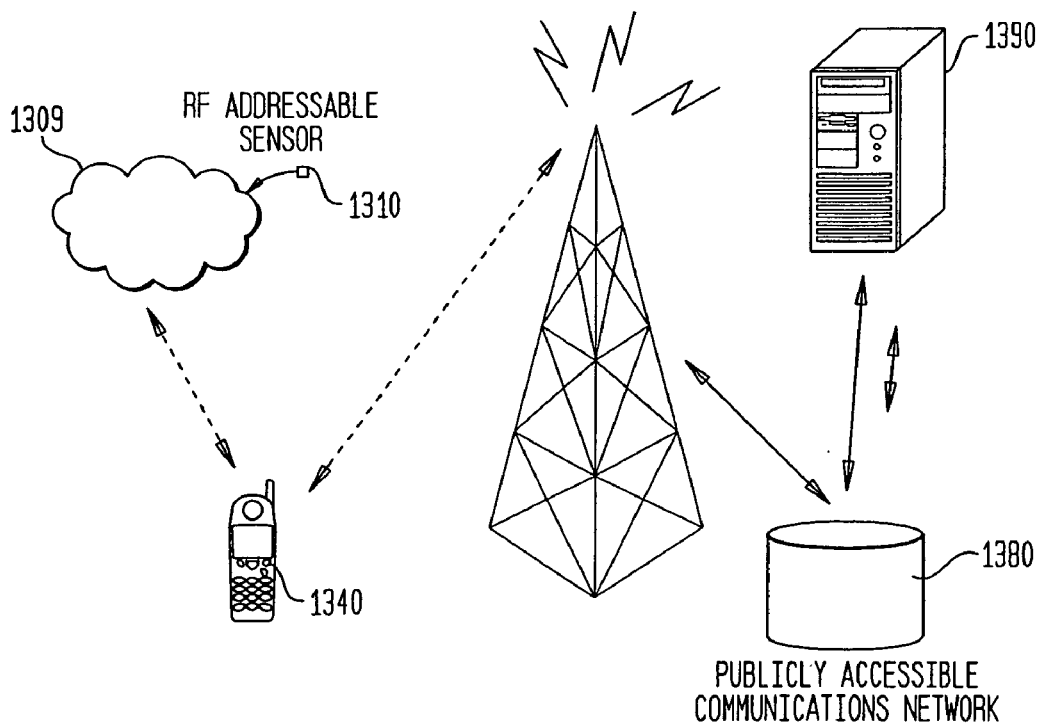

FIG. 13B depicts a block diagram of a network-based food testing application, according to an example embodiment of the present invention.

Figure 14:
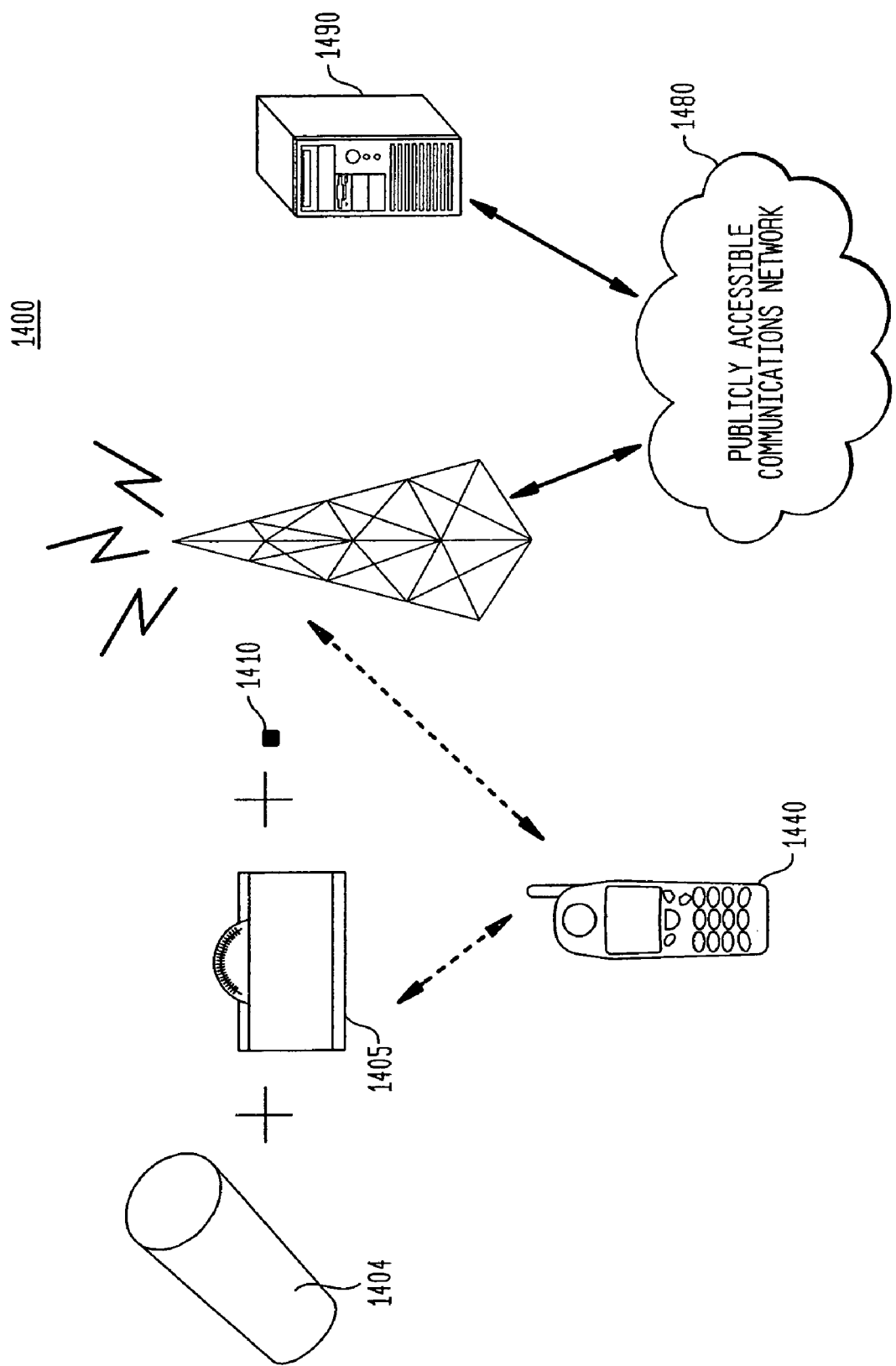

FIG. 14 depicts a block diagram of an example application of a sensor network for identifying potential interactions among prescribed drugs, according to an example embodiment of the present invention.

Figure 15:
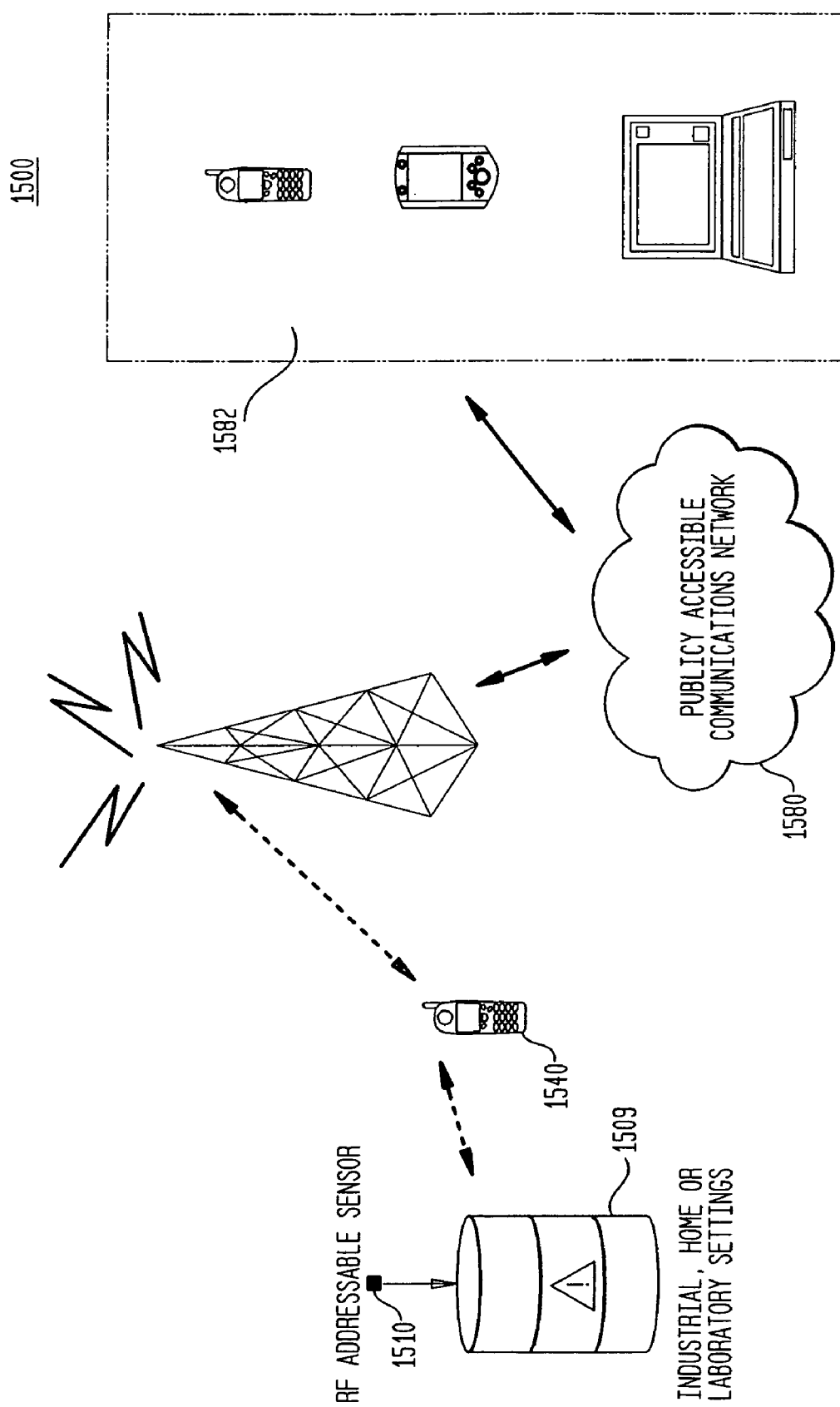

FIG. 15 depicts a block diagram of an example application of a sensor network for remote sensing of hazardous conditions, according to an example embodiment of the present invention.

Figure 16:
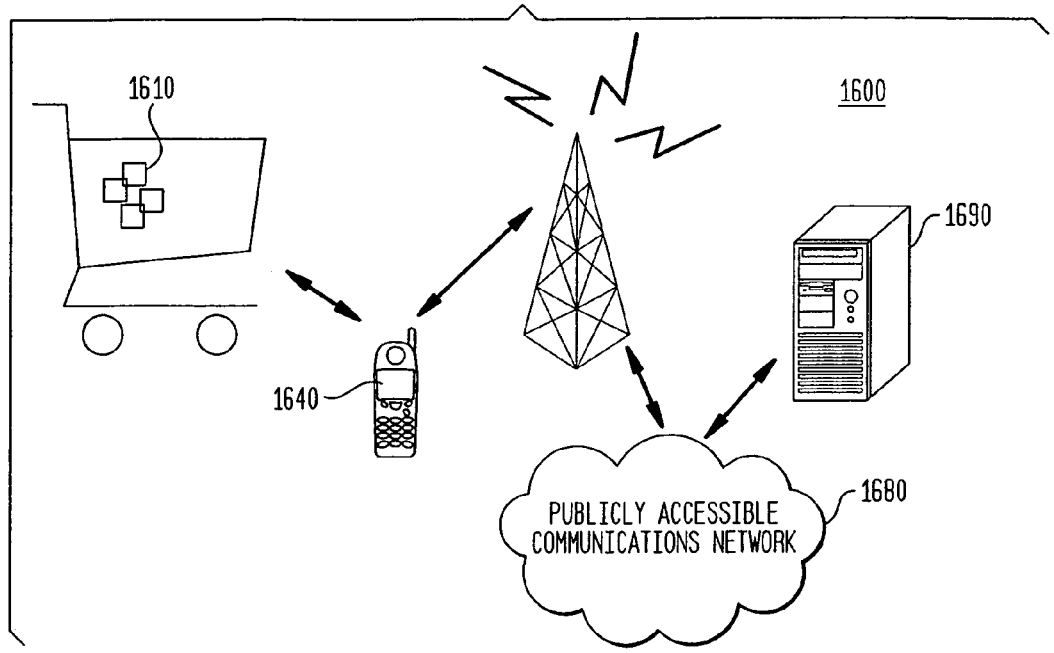

FIG. 16 depicts a block diagram of an example application of a sensor network for shopping, according to an example embodiment of the present invention.

Figure 17:
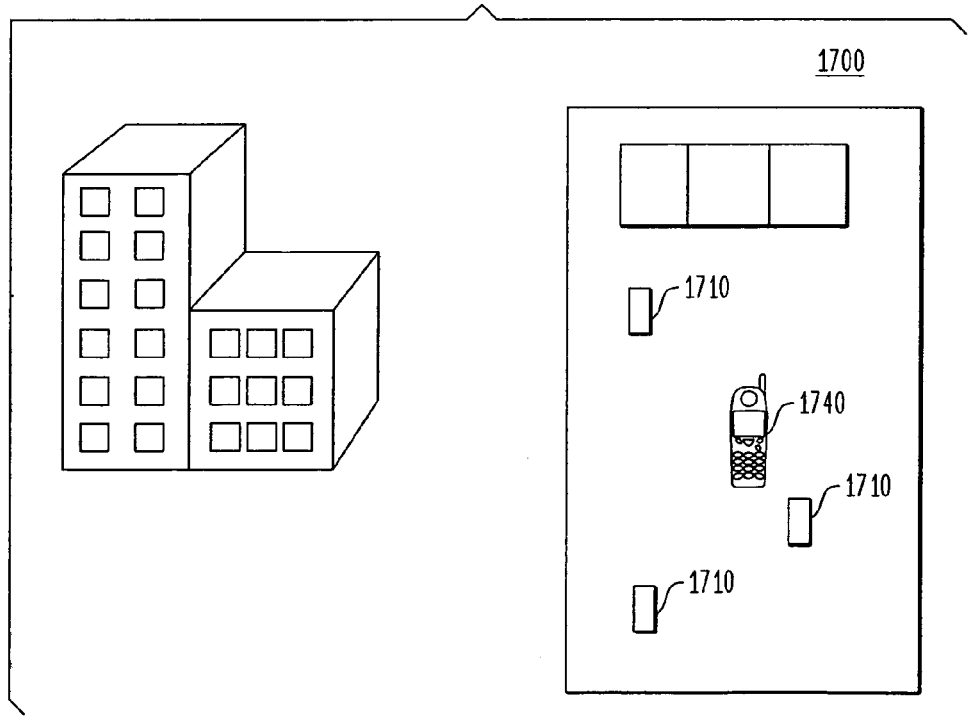

FIG. 17 depicts a block diagram of an example application of a sensor network for monitoring structures, according to an example embodiment of the present invention.

The present invention will now be described with reference to the accompanying drawings. In the drawings, like reference numbers can indicate identical or functionally similar elements. Additionally, the left-most digit(s) of a reference number may identify the drawing in which the reference number first appears.

DETAILED DESCRIPTION OF THE INVENTION

1. Architectural Embodiments of the Present Invention

Various embodiments for RF addressable sensor networks, RF addressable sensors, and RF addressable sensor readers are described in the following subsections. These embodiments are provided for illustrative purposes, and it should be understood that the invention is not limited to the particular embodiments described below. Alternative embodiments for RF addressable sensor networks, RF addressable sensors, and RF addressable sensor readers will be apparent to persons skilled in the relevant arts based on the teachings herein, including those with equivalents, combinations, modifications, greater or fewer components, etc. It is to be understood that such alternative embodiments are within the scope and spirit of the present invention.

1.1 RF Addressable Sensor Network

Figure 1:
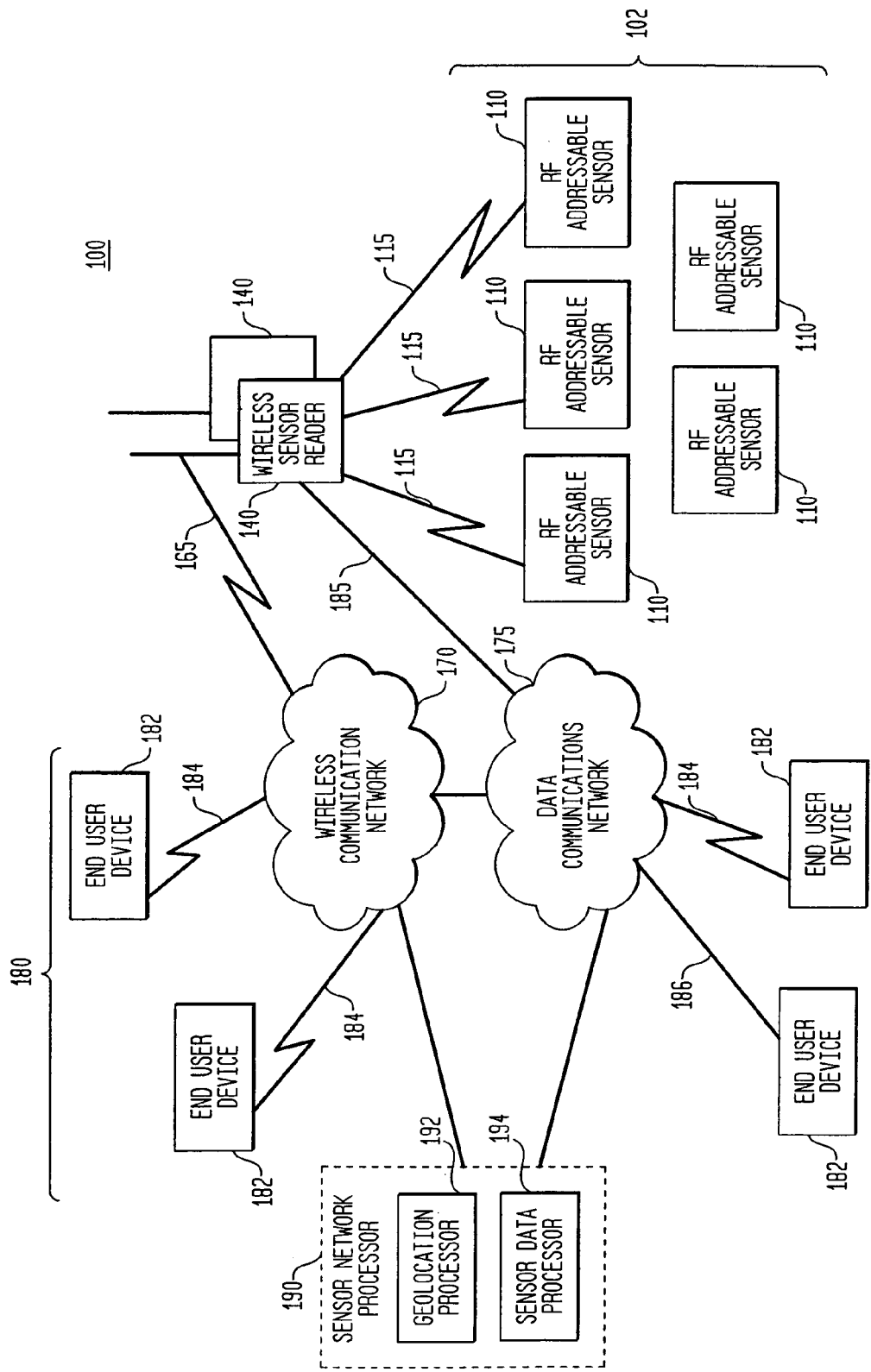
FIG. 1 is a block diagram of an illustrative RF addressable sensor network according to an embodiment of the present invention.

FIG. 1 is a block diagram of an illustrative RF addressable sensor network 100 for monitoring, detecting, and geolocating RF addressable sensors, according to an embodiment of the present invention. Network 100 includes a population of RF addressable sensors 102, one or more wireless addressable sensor readers 140, and a communications network 180. In an embodiment of the present invention, communications network 180 is a publicly accessible communications network. In another embodiment, communications network 180 is a private network or a hybrid network including public and private portions. Communications network 180 includes a wireless communications network 170 and/or a data communications network 175. While FIG. 1 depicts communications network 180 as including a wireless and a data communications network, persons skilled in the relevant art(s) will recognize that other network architectures could be used with the present invention.

In an embodiment, end user devices 182 may be coupled to communications network 180. End user devices 182 include logic for bi-directional communication with the communications network 180. End user devices 182 may be present to initiate a request for sensor data from RF addressable sensors 102 by making the request to readers 140 over network 180. In an embodiment, end user devices 182 also include logic to process received sensor data. For example, a user device 182 may include features of a processor 190, which is further described below. Thus, in an embodiment, a user device 182 may both initiate a request for sensor data and receive and process the resulting sensor data. End user devices 182 can communicate with communications network 180 via a wireless link 184 or a wired link 186. In an alternate embodiment, network 100 also includes a sensor network processor 190.

According to embodiments of the present invention, the population of RF addressable sensors 102 may include any number of one or more RF addressable sensors 110. RF addressable sensors 110 integrate RFID tag functionality and sensor functionality. RF addressable sensor 110 may be attached to the exterior of an item, inserted into an item (e.g., immersed in a liquid), or may be stand-alone.

Wireless sensor reader 140 includes logic to interrogate the population of RF addressable sensors 102 and logic to read sensor data and RFID tag data transmitted by the RF addressable sensors 110. In an embodiment, wireless sensor reader 140 also includes logic to process the received sensor data. Wireless sensor reader 140 can be any wireless device capable of communicating via an air interface protocol with the population of RF addressable sensors 102. In embodiments of the present invention, wireless sensor reader 140 could be a wireless phone, a personal digital assistant (PDA), a computer having wireless communications capabilities, or other type of mobile, handheld, and/or computing device.

According to the present invention, signals 115 are exchanged between the wireless sensor reader 140 and the population of RF addressable sensors 102 according to one or more protocols. Signals 115 are wireless signals, such as radio frequency (RF) transmissions. In an embodiment of the present invention, reader 140 and the population of sensors 102 communicate via a single protocol for both RFID tag communications and sensor communications. In an alternate embodiment, reader 140 and the population of sensors 102 communicate via a first protocol for RFID tag communications and via a second protocol for sensor communications. Examples of protocols used for RFID tag communications are described in the following co-pending U.S. patent applications, each of which is incorporated by reference in its entirety: application Ser. No. 10/072,984, filed Feb. 12, 2002, entitled "Radio Frequency Identification Architecture;" application Ser. No. 10/687,690, filed Oct. 20, 2003, entitled "Method for the Efficient Reading of a Population of Radio Frequency Identification Tags with Unique Identification Numbers Over a Noisy Air Channel;" and application Ser. No. 10/693,687, filed Oct. 27, 2003, entitled "Optimization of a Binary Tree Traversal with Secure Communications." The present invention is also applicable to any other types of communication protocols between tags and readers otherwise known or yet to be developed.

In an embodiment of the present invention, signals 165 are exchanged between the wireless sensor reader 140 and the wireless communication network 170 according to one or more protocols. Signals 165 are typically RF signals. As can be appreciated by a person skilled in the relevant art(s), the communications protocol used between reader 140 and wireless network 170 can be any wireless air interface protocol, such as used in IS-41 or GSM wireless communications networks, for example.

In an alternate embodiment, wireless sensor reader 140 can also communicate to the data communications network 175 via interface 185. Interface 185 is a wired interface. For example, when wireless sensor reader 140 is a computer having wireless capabilities, sensor reader 140 may access the Internet via interface 185 using TCP/IP. As can be appreciated by a person skilled in the relevant art(s), the communications protocol used between reader 140 and data communications network 175 can be any data communications protocol.

In an embodiment of the present invention, wireless network 170 is a publicly accessible network, such as a switched telephone network supporting wireless communications. In an alternate embodiment, wireless network 170 may be a private network. Wireless network 170 may be coupled to a publicly accessible data communications network 175. Publicly accessible data communications network 175 can be a public switched telephone network or a public data network such as the Internet. In addition, data communications network 175 can be connected to other public or private networks as would be appreciated by persons skilled in the relevant art(s).

Sensor network processor 190 receives sensor data over network 180, and processes the data. Furthermore, in an embodiment, processor 190 transmits the processed data back over network 180 to reader 140, for example. Sensor network processor 190 includes a geolocation processor 192 and a sensor data processor 194. Sensor network processor 190 may be a stand-alone system or may be distributed across multiple systems. Geolocation processor 192 includes logic to receive data from one or more RF addressable sensors 110 and to perform GPS and/or non-GPS geolocation of the RF addressable sensors 110 based on the received data and/or signals. In GPS based geolocation, location is determined using signals provided to wireless sensor readers 140 via geo-stationary satellites. A limitation of GPS based geolocation is that signals are not available if the device is shielded (e.g., underground, in a building, etc.). In non-GPS based geolocation, location is determined by triangulation based on transmission systems as reference points (e.g., mobile base stations) and time to signal calculations. In this manner, cell phone towers can geolocate wireless sensor readers 140 through calculations done by processor 190. Similarly, wireless sensors readers 140 may be used as a basis to identify the precise location of individual sensors 110 by triangulation and synchronization of internal clocks. Since either the location of cell phone towers and/or wireless sensor readers is usually known and can include GPS coordinates, precise geolocation of sensors can be achieved using either GPS, non-GPS or hybrid systems.

For more information concerning geolocation, see U.S. Pat. No. 6,031,454, filed Nov. 13, 1997, entitled "Worker-Specific Exposure Monitor and Method for Surveillance of Workers," which is incorporated herein by reference in its entirety.

Sensor data processor 194 includes logic to receive sensor data from one or more RF addressable sensors 110, perform processing on the received data, and communicate information based on the processing to wireless reader 140 or an end user device 182. Sensor network processor 190 is coupled to the wireless communications network 170 and/or the data communications network 175.

1.2 RF Addressable Sensor

Figure 2:
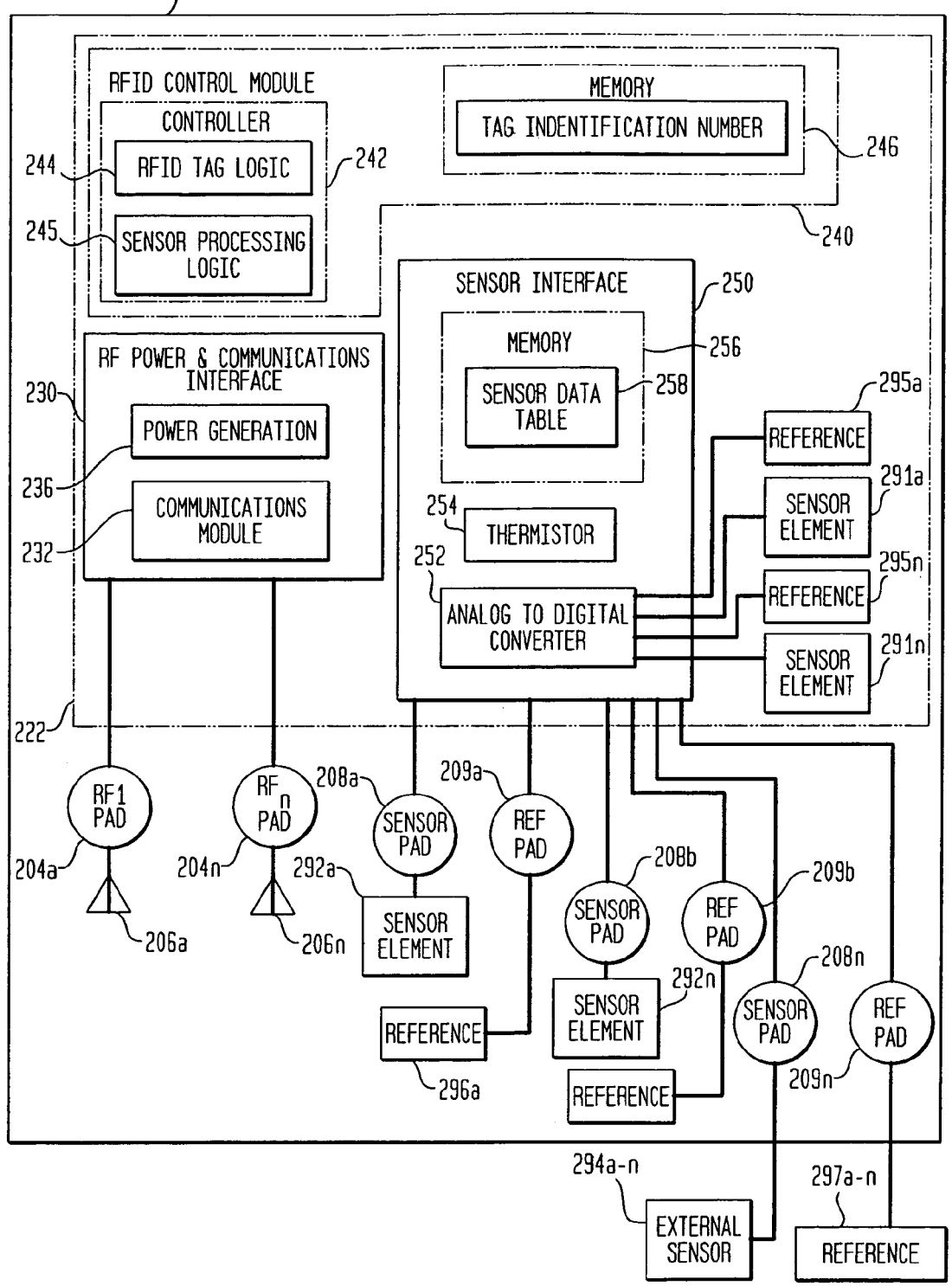
FIG. 2 is a block diagram of an illustrative RF addressable sensor according to embodiments of the present invention.

FIG. 2 is a block diagram of a radio frequency (RF) addressable sensor 210, according to an embodiment of the present invention. RF addressable sensor includes RFID tag functionality integrated with sensor functionality.

Radio frequency addressable sensor 210 includes an integrated circuit 222, a plurality of RF pads 204a through 204n, and a plurality of antennas 206a through 206n. These components are mounted or formed on a substrate 202. RF addressable sensor 210 also includes a plurality of sensor elements 291a–291n, 292a–292n, and 294a–294n.

Sensor elements may be included in integrated circuit 222, on substrate 202, external to substrate 202, or in any combination of the above. As shown in FIG. 2, sensor elements 291a–n are included as a component in integrated circuit 222. Sensor elements 292a–n are included on the substrate 202. Any sensor element that is compatible with the fabrication of RF addressable sensor 210 can be used. In an embodiment of the invention, sensor elements 292a–n can be thin film sensor elements that are deposited, printed, or directly assembled onto substrate 202. Sensor elements 294a–n are external to the substrate 202. If the sensor element is located on the substrate (collectively sensor elements 292) or external to the substrate (collectively sensor elements 294), the sensor element will be coupled to one or more of the plurality of sensor pads 208a through 208n (collectively sensor pads 208).

The structure of sensor pads 208 depends on the type of sensor element coupled to the sensor pad 208. In an embodiment of the present invention, sensor pads 208 are metal. However, certain biological sensor elements consist of soft materials. When coupling to metal sensor pads 208, the potential exists for these sensor elements to be pierced. In an alternate embodiment of the present invention, one or more sensor pads are soft sensor pads. These soft sensor pads provide a transition from a metal connection layer for coupling to the integrated circuit components to a soft connection layer for coupling to the sensor element. By using a soft transition method any type of external sensor element can be coupled to substrate 202. For example, doped inks or conductive polymers can be used to couple and bond substrate 202 to an integrated sensor as described below. The integrated sensor may be fabricated using other micro or nanofabrication techniques, thereby providing a means for an sophisticated integrated wireless sensor to be produced at a very low cost and for many different market applications.

Because of this flexible architecture, various types of sensor elements can be implemented in RF addressable sensor 210. An RF addressable sensor 210 may include only one type of sensor element or may include a combination of different types of sensor elements. Examples of sensor elements include: gas sensor elements that detect the presence of chemicals, such as those associated with drugs or precursor or trace chemicals of explosives such as Pentaerythritol Tetranitrate (PETN) and Hexahydro-1,3,5-triazine (RDX); temperature sensor elements that generate information indicating ambient temperature; accelerometers that generate information indicating movement or vibration; optical sensor elements that detect the presence (or absence) of light; pressure sensor elements that detect various types of mechanical pressures; tamper sensor elements that detect efforts to destroy or remove the sensor from affixed items; electromagnetic field sensor elements, radiation sensor elements; and biochemical sensor elements. However, this list is not exhaustive. RF addressable sensor 210 may include other types of sensor elements or combinations thereof, as would be apparent to persons skilled in the relevant art(s).

Sensor elements 291a to 291n are sensors that can be fabricated directly on the chip surface as part of integrated circuit 222. For example, these include sensors for temperature change, radiation, electrical changes, field effects and motion. Sensor elements 292a to 292n may be a number of different sensor types such as a chemical sensors, biological sensors, etc. In an embodiment, sensor element 292a may include of a plurality of special thin film elements such as polymers. For example, in chemical sensor elements, chemicals present in the air are absorbed differently by each of the thin film elements, changing the resistance of each and creating a characteristic electronic signature. Because many types of detectors can be added, this technology can be designed to recognize a wide range of chemicals. It should be noted that hybrid systems are also possible. For example, embedded passives may be used to create some of the electronic functionality on the chip and combined with sensor functionality.

In an alternate embodiment, one or more of the antennas 206 may be used as sensor elements. For example, the antenna could operate as an on-off sensor. As the antenna absorbs material to be sensed, the antenna becomes detuned and the tag stops operating. Thus, when the tag shuts off, the material has been sensed. In this embodiment, the antennas acting as sensor elements are coupled to both an RF pad 204 and a sensor pad 208. In an alternate embodiment, RF pads 204 are coupled to both the RF power and communications interface 240 and the sensor interface 250.

In an embodiment of the present invention, RF addressable sensor 210 is or includes a micro-electro-mechanical system (MEMS). In an embodiment, sensor elements can include mechanical and electromechanical devices "micromachined" on a common or separate substrate with the remaining components of the RF addressable sensor 210. In this embodiment, the remaining electronic components could be fabricated using conventional integrated circuit technology. For example, in a MEMS RF addressable sensor, one or more sensor elements can contain microcantilever devices.

In an alternate embodiment, the sensor elements 294a–294n are external to substrate 202 and can be fabricated using MEMS technology and attached to substrate 202, while the components included on substrate 202 can be fabricated using conventional technology. This allows any type of sensor to be coupled with an RFID tag.

Figure 2A:
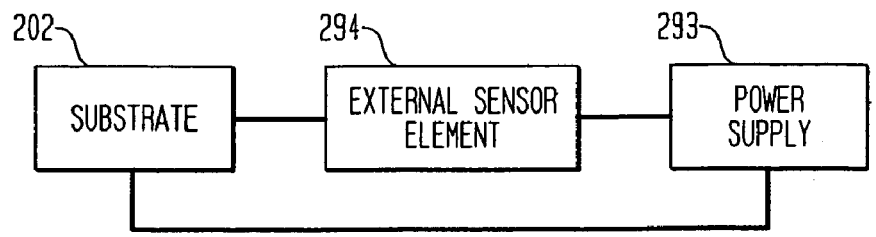
FIG. 2A is a block diagram of an illustrative RF addressable sensor having an external sensor element according to embodiments of the present invention.

FIG. 2A is a block diagram of an RF addressable sensor 210 having an external sensor element according to embodiments of the present invention. External sensor element 294 may be coupled to an independent power supply 293. Substrate 202 may also or alternatively be coupled to independent power supply 293. In an embodiment, power supply 293 is a disposable battery or a photovoltaic cell. Thus, sensor element 294 does not require periodic "power" signals from the wireless reader. In an embodiment, sensor element 294 includes a memory.

An advantage of the RF addressable sensor configuration of FIG. 2A is that the wireless components and geolocation features are provided by the RFID tag and cell phone combination thereby reducing the cost and making it suitable for sensor networks. An example of an application is a homeland security network with sensors that are dispersed by airplane over certain areas together with low cost readers. If a hazard is detected, sufficient power is present at the sensor level to send a "wake up" signal to a nearby reader. The reader then geolocates itself and the sensor and relays the information to a remote processor 190. Cross validation of sensor events may then be achieved by activating and reading other sensors in the same geographical area. A further advantage is that the present invention can be used in combination with sensors that require more power than is available on an RFID tag. In addition, sensor elements that require very different manufacturing processes than the RFID tag can also be used in the present invention.

In an embodiment of the present invention, as shown in FIG. 2, RF addressable sensor 210 optionally includes a plurality of reference elements 295a–295n, 296a–296n, and 297a–297n. Similar to the sensor elements, reference elements may be included in integrated circuit 222, on substrate 202, external to substrate 202, or in any combination of the above. As shown in FIG. 2, reference elements 295a–295n are included in integrated circuit 222; reference elements 296a–296n are included on substrate 202; and reference elements 297a–297n are external to substrate 202. A sensor element need not have a reference element. If the reference element is located on the substrate (collectively reference elements 296) or external to the substrate (collectively reference elements 297), the reference element will be coupled to one or more of the plurality of reference pads 209a through 209n (collectively reference pads 209).

Reference elements allow for the cross validation of sensor data and establish baselines. This is important for chemical measurements, for biological sensors, and for any sensor situation where there are two or more variables and at least one of the variables is dependent or proportional to the other.

In an embodiment of the present invention, a sensor element may have a plurality of associated reference elements. In an embodiment, a reference element provides a baseline and/or calibrated value to which a sensor element can be compared either internally or externally. In an embodiment, reference data can be transmitted by the RF addressable sensor to the wireless sensor reader or to the network sensor processor for calibration of the sensor elements.

As shown in the embodiment of FIG. 2, integrated circuit 222 includes a RF power and communications interface 230, a sensor interface 250, and an RFID control module 240. Sensor interface 250 includes a digitizer or an analog to digital converter (ADC) 252. ADC 252 receives analog signals from sensor elements and converts the analog signal into a corresponding digital signal. ADC 252 can be coupled directly to sensor elements implemented in integrated circuit 222 and is coupled to other sensor elements 292 and 294 via sensor pads 208. In an embodiment, a filter (not shown) may be used between the sensor element and ADC 252.

In an embodiment of the present invention, sensor interface 250 optionally includes one or more thermistors 254. Thermistor 254 is a device that has an electrical resistance that varies predictably with temperature. Thermistor 254 provides a correlation point for data obtained from a sensor element. Because temperature is a generally known variable, including a thermistor in RF addressable sensor 210 allows the sensor 210 to use temperature as a basis for comparison or allows a sensor element output value to be adjusted based on temperature. This adjustment can occur internally or externally at the wireless sensor reader 140, end user device 182, and/or network sensor processor 190.

In an embodiment of the present invention, thermistor 254 is made of a material such as a metal-oxide that has a resistance that changes in a linear fashion according to temperature. Hence, at a given temperature, the thermistor has a certain value that can be correlated precisely to a given temperature. The calibration of thermistor 254 can be done in batches after the chip is microfabricated. Calibration can be achieved by bringing the chip to a set temperature and programming into the chip the corresponding value. This process can be repeated at two different temperatures, thereby providing the reference in memory.

In an embodiment of the present invention, thermistor 254 is made of a non-linearly changing material. In this embodiment, additional calibration points are used. As would be appreciated by persons skilled in the relevant art(s), other implementations of thermistor 254 can be used in the present invention.

In an embodiment, sensor interface 250 may optionally include a memory 256. Memory 256 stores information used by RF addressable sensor 210 to process sensor data received from sensor elements. The information may be stored permanently or temporarily. In an embodiment of the present invention, memory 256 is a programmable memory. The stored information may be used internally by the RF addressable sensor 110 or may be communicated for use externally by the wireless sensor reader 140, an end user device 182, and/or the network sensor processor 190.

In an embodiment, memory 256 stores a sensor data table 258. The sensor data table 258 is configured to store data related to all or a subset of sensor elements supported by the RF addressable sensor 210. For example, the sensor data table may store a sensor element identification number, a preferred read time, spacing interval between reads, and/or sensor element specific data for all or a subset of sensor elements.

Using this approach a universal sensor platform is created based on RFID technology by allowing wireless devices such as phones to become "smart" sensor reader devices. In an embodiment, a wireless device such as a phone is modified to include RFID-sensor tag reader functionality, as described herein. In an embodiment, when a sensor 110 having data table 258 is activated by wireless sensor reader 140, the sensor 110 identifies itself (e.g., by providing its identification number) and provides the cell phone reader with the necessary information for analyzing the sensor output. In an embodiment, sensor data table 258 also includes sensor handling information that is communicated to reader 140. For example, if sensor 110 is to detect a specific allergen in food, a complete step-by-step testing protocol can be provided and can be displayed directly on the screen of the phone or reader device 140. In another embodiment, some or all of the necessary information to handle and analyze the sensor is retrieved from processor 190.

Software may also be downloaded directly and transparently into the cell phone or reader 140 to "train" the wireless device to recognize and analyze that given type of RFID-sensor. This information may be stored permanently or temporarily in wireless device 140. When the necessary processing and analysis information is downloaded from a remote location, only the ID of the RFID-sensor is necessary, providing a highly streamlined solution for universal sensor analyses for wireless devices such as cell phones. In another embodiment, hybrid systems can be provided whereby only a basic sensor analysis protocol can be downloaded into the cell phones and the sensor data processing is done remotely. This situation is particularly applicable where complex multivariate analyses of sensor data are required. Phones may also include in permanent memory a summary table with the necessary IDs to recognize any type of sensor. The above described method allows an ordinary wireless device to instantly become a "smart" device for any type of sensor Integrated circuit 222 can accommodate multiple antennas 206a through 206n. This allows RF addressable sensor 210 to have a variety of antenna configurations on substrate 202. For example, wireless sensor reader 140 (shown in FIG. 1) may operate at a different frequency or have different directivity than conventional RFID readers. Therefore, RF addressable sensor 210 may have one or more antennas configured to communicate with a conventional RFID reader and one or more antennas configured to communicate with wireless sensor reader 140.

The RFID control module 240 controls RF communications between the RF addressable sensor 210 and wireless sensor reader 140. RFID control module includes a controller 242 and a memory 246. Controller 242 includes RFID tag logic 244 to respond to RFID tag interrogation and read communications by the wireless sensor reader 140 or another tag reader and logic to control the operating state of the RFID tag components of the RF addressable sensor. For more information concerning interrogation of tags, and more generally, communication between an RFID reader and a population of tags in accordance with an embodiment of the present invention, see U.S. Pat. No. 6,002,344, entitled, "System and Method for Electronic Inventory" which is incorporated herein by reference in its entirety, and the following co-pending U.S. patent applications, each of which is incorporated by reference in its entirety: application Ser. No. 09/323,206, filed Jun. 1, 1999, entitled "System and Method for Electronic Inventory"; application Ser. No. 10/072,855, filed Feb. 12, 2002, entitled "Method, System and Apparatus for Binary Traversal of a Tag Population" (Publication No. 0149481-A1); and application Ser. No. 10/073,000, filed Feb. 12, 2002, entitled "Method, System and Apparatus for Communicating with a RFID Tag Population."

Controller 242 may optionally include sensor processing logic 245 to process sensor data obtained by sensor elements. Memory 246 stores information used by the RF addressable sensor when operating as a RFID tag. Memory 246 may be separate or integrated with memory 256 of the sensor interface. The information may be stored permanently or temporarily. Memory 246 stores the tag identification number for the RF addressable sensor 210. In an embodiment of the present invention, the tag identification number indicates the type of sensor elements included in the RF addressable sensor 210.

RF Power and Communications Interface 230 includes a communications module 232 and a power generation module 236. Communications module 232 is coupled to antennas 206 to provide bi-direction communication with a wireless RF addressable sensor reader. In an alternate embodiment, communication module 232 provides bi-directional communication with a conventional RFID reader in addition to the wireless RF addressable sensor reader. In an embodiment, power generation module 236 provides integrated circuit 222 with an operational voltage based on the RF energy transmitted by wireless sensor reader 140 and received by the corresponding RF addressable sensor 110. In another embodiment, power generation module 236 may also include a battery or other power source. Alternatively, power generation module 236 may only include a battery or other power source. When present, the power source provides the operational voltage for integrated circuit 222. In addition, the power generation module 236 may provide operational voltage for sensor elements 292a–n and/or 294a–n. For example information concerning power generation in an RFID tag, see U.S. patent application Ser No. 10/383,537, filed Mar. 10, 2003, entitled, "Efficient Charge Pump Apparatus" which is incorporated herein by reference in its entirety.

In an embodiment, when a power source is present, the RF addressable tag may include logic to activate the reader when certain conditions are sensed, on the occurrence of a pre-defined event, and/or at pre-defined intervals. As would be appreciated by persons skilled in the art, many RFID tag communications protocols can be used to activate the reader according to the present invention.

1.3 Wireless RF Addressable Sensor Reader

Figure 3:
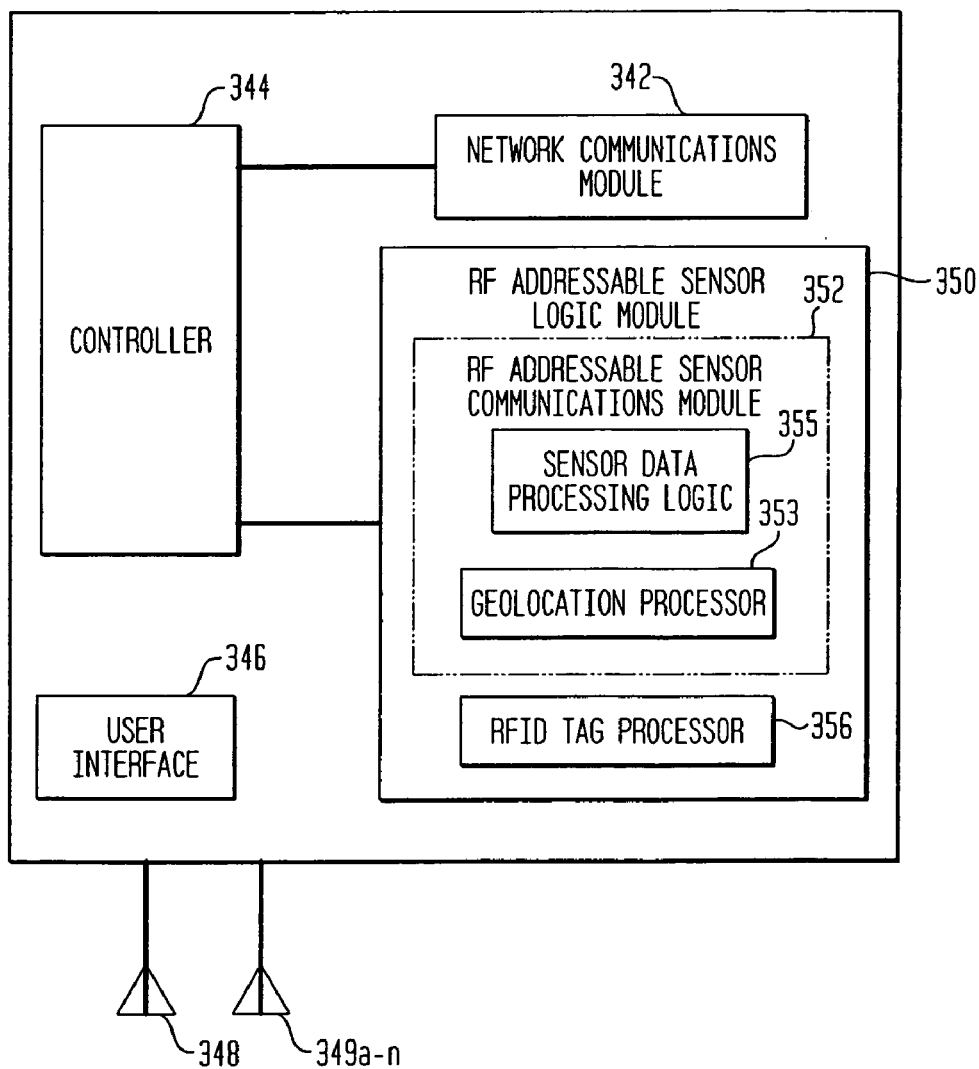
FIG. 3 is a block diagram of a wireless sensor reader according to embodiments of the present invention.

Example embodiments for wireless sensor reader 140 are described in this section. FIG. 3 is a block diagram of a wireless sensor reader 340 according to example embodiments of the present invention. Wireless sensor reader 340 includes a network communications module 342, a controller 344, a user interface 346, and an RF addressable sensor logic module 350. Wireless sensor reader 340 also includes one or more antennas. Antenna 348 is configured for communication with wireless network 170. Antenna 348 is included when wireless reader 340 is integrated with a wireless communications device. In an embodiment of the present invention, antenna 348 is also configured for communication with the population of RF addressable sensors. Antennas 349a–n are included when antenna 348 does not support communication with the population of RF addressable sensors. In this embodiment, antennas 349 are configured to communicate with the RF addressable sensors 110. In an alternate embodiment, network antenna 348 can be removed (e.g., unscrewed) from reader 340 and replaced with an RFID antenna 349 for communication with the population of sensors 102.

Controller 344 includes logic to coordinate and control the operation of the components of wireless sensor reader 340.

User interface 346 provides a mechanism for the user of the wireless sensor reader 340 to access and interact with sensor information and/or initiate a read of one or more sensors 110. User interface 346 may include a display and/or keypad for entering data (e.g., the numerical keypad of a wireless phone). In an alternate embodiment, user interface 346 includes a standalone button for initiating sensor reads and/or processing. In addition, the wireless sensor reader 340 includes a display for displaying data obtained from RF addressable sensors 110. In an embodiment, the wireless sensor reader 340 also includes an alarm for indicating when certain thresholds are reached or certain conditions are detected by an RF addressable sensor.

A user may alternatively initiate sensor processing by entering a pre-defined sequence of characters via a key pad (e.g., by entering *2222). Alternately, a user could initiate sensor processing by highlighting or activating an option provided through a display or by a predefined voice command.

Network communications module 342 includes one or more transmitters and receivers for communicating with the data communications network 175 and/or wireless communications network 170. In an embodiment of the present invention, wireless sensor reader 340 communicates with wireless network 170 via network antenna 348. Accordingly, network communications module 342 includes a wireless interface coupled to the antenna 348. In an alternate embodiment of the present invention, wireless sensor reader 340 communicates with a publicly accessible data communications network 175 via a wired connection. In this embodiment, network communications module 342 includes a wired network interface. If both types of communications are supported, network communications module 342 will include both a wireless interface and a wired interface.

RF addressable sensor logic module 350 includes an RF addressable sensor communications module 352 and an RFID tag processor 356. Wireless sensor reader 340 communicates with the population of RF addressable sensors 102 via either the network antenna 348 or via one or more RFID antenna(s) 349a–349n. If wireless sensor reader 340 communicates with the population of RF addressable sensors via one or more RFID antenna(s) 349a–n, RF communications module 352 will include one or more transmitters and receivers coupled to antennas 349. As will be appreciated by a person skilled in the relevant art(s), RF communications module 352 may be implemented in hardware, software, firmware, or in combination thereof.

RFID tag processor 356 includes logic to interrogate and read RFID tag information from RF addressable sensors 110. As will be appreciated by a person skilled in the relevant art(s), RFID tag processor 356 may be implemented in hardware, software, firmware, or in combination thereof.

RF addressable sensor communications module 352 includes sensor data processing logic 355 and geolocation processing logic 353. Sensor data processing logic 355 is configured to request a read of one or more addressable sensors 110 based on input from a user, after a certain interval of time, and/or upon the occurrence of a pre-defined event. Sensor data processing logic 355 is also configured to process received sensor data.

Geolocation processor 353 is optional, and when present, includes algorithms to perform GPS based geolocation and/or non-GPS based geolocation. In an embodiment, sensor reader 340 serves as a geolocation beacon for RFID-sensors in synchrony with other readers. In an embodiment, the antenna serves as a means for directional geolocation of RFID sensors.

FIGS. 4A–C depict block diagrams of example configurations for a wireless sensor reader 440. Each configuration depicts various ways in which RF addressable sensor logic module 350 and RFID antennas 349a–n may be incorporated into a device 430. Device 430 can be an existing wireless device such as a wireless phone or PDA. In an alternate embodiment, device 430 is a device designed specifically to support communicating with RF addressable sensors 110 and with a communications network such as a wireless phone network or the Internet.

In FIG. 4A, RF addressable sensor logic module 350 is integrated into device 430. In this embodiment, wireless sensor reader 440 communicates with both the wireless network 170 and the population of RF addressable sensor tags via antenna 448. In an embodiment of the present invention, module 350 is built into device 430. In an alternate embodiment, device 430 includes a programmable processor. The logic for module 350 can be downloaded and stored in the programmable processor. The logic can be downloaded via the air interface, an infrared port, a data connection through the accessory port, or via any other interface or link capable of transferring data to device 430.

In FIG. 4B, RF addressable sensor logic module 350 is integrated into device 430, as discussed in reference to FIG. 4A. However, in this embodiment, one or more antennas 449a–n are already included, or added onto device 430 for communication with the population of RF addressable sensors 102. Note that for this configuration, antenna 448 is optional and is not included if wireless sensor reader 340 only communicates with a data communications 175 network via a wired connection.

In FIG. 4C, RF addressable sensor logic module 350 is external to device 430 and is attached to device 430 via interface 435. For example, interface 435 could be an accessory port, an infrared port, or any other interface or port capable of transferring data to and from device 430 such as a wireless phone data/software interface. For example, module 350 may be a snap-on and/or plug-in module to device 430. Various antenna configurations are supported with this embodiment. In an embodiment, existing antenna 448 supports communication with both the network 170 and the population of sensors 102. In an alternate embodiment, additional antennas 449 for communicating with the population of sensors 102 are attached to external module 350. In another alternate embodiment, additional antennas 449 for communicating with the population of sensors 102 are attached to device 430. As would be appreciated by a person skilled in the relevant art(s), other configurations for wireless sensor reader 440 are possible.

2. RF Addressable Sensor Network Methods 2.1 RF Addressable Sensor Read Communications FIG. 5 is a flowchart of a method 500 for RF addressable sensor read communications from the perspective of a wireless sensor reader. Method 500 will be described with continued reference to FIGS. 1 and 3. Note that some steps shown in the flowchart do not necessarily have to occur in the order shown.

Method 500 begins with step 510. In step 510, a read of one or more RF addressable sensors is initiated. In an embodiment of the present invention, sensor data processing logic 355 includes logic that periodically initiates sensor read communications. For example, sensor data processing logic 355 may automatically initiate a sensor read every 15 minutes. A sensor read may also be initiated manually via the user interface 346 of wireless sensor reader 140/340. For example, a user may initiate a read by activating a display icon or option. In an embodiment, a user may initiate a read by pressing a series of keys on the device keypad (e.g., *2222) or by pressing a specifically configured sensor read button. Alternatively, if the device supports voice activated commands, the user may initiate a sensor read by speaking the appropriate command.

In addition, a sensor read can be initiated remotely over data communications network 175 or the wireless network 170. FIG. 6 depicts a method 602 for remotely initiating a sensor read according to embodiments of the present invention. Method 602 begins with step 603. In step 603, the wireless sensor reader 140/340 receives a connection signal from an end user device 182. As would be appreciated by a person skilled in the relevant art(s), the type and format of the connection signal depends upon the implementation of the end user device 182 and the wireless sensor reader 140/340. For example, if the wireless sensor reader 140/340 is also a wireless telephone device, the connection signal may be a telephone call by the end user device to the wireless sensor reader. Alternatively, end user device may be a data terminal. In this example, the connection signal may be any type of data communications connection signals.

In step 605, the wireless reader 140/340 connects to the end user device over a communications network.

In step 607, the wireless reader 140/340 receives initiation signal(s) from the end user device. As would be appreciated by a person skilled in the relevant art(s), the type and format of the initiation signal(s) depends upon the type and format of the connection signal. If a telephone connection is established, then the initiation signals may be a series of dual tone multifrequency (DTMF) signals or a voice command. Control then proceeds to step 520.

Returning to FIG. 5, in step 520, the wireless sensor reader 140/340 communicates RF signals to one or more addressable sensors 520. These RF signals serve a dual purpose. They initialize the RF addressable sensors for communications and provide operating power to the sensors.

Based on the details provided during read initiation, the wireless sensor reader 140/340 may perform a sensor read of the entire population of RF addressable sensors 102 or may perform a read of a specific set of RF addressable sensors. In step 530, the reader determines whether to read the entire RF addressable sensor population 102 or one or more specific RF addressable sensors 110. If the entire population is to be read, operation proceeds to step 550. If one or more specific sensors 110 are to be read, operation proceeds to step 540.

For example, a user may obtain (e.g., purchase) a batch of RF addressable sensors. The user may store the tag identification numbers associated with each RF addressable sensor in the wireless sensor reader prior to initiating a read of the sensors. The reader can then isolate only those specific RF addressable sensors stored in the wireless sensor reader.

In step 540, RFID tag processor 356 isolates (e.g., singulates) the specific RF addressable sensor 110 to be read. Processor 356 may isolate a sensor 110 through an interrogation protocol, or other mechanism. For details on methods for isolating a specific tag, see pending U.S. Application entitled, "Radio Frequency Identification Architecture," referenced above. As would be appreciated by persons skilled in the relevant art(s), other protocols and methods for reading and isolating tags can be used with the present invention.

In step 542, the wireless sensor reader 140/340 instructs the specific RF addressable sensor 110 to obtain sensor data. This can be done via a predefined command. In an alternate embodiment, RF addressable sensor 110 automatically signals sensor data to wireless sensor reader 140/340 upon being isolated. In this embodiment, step 542 is optional.

In step 544, the wireless sensor reader 140/340 receives the sensor data from the RF addressable sensor 110. Sensor data can include sensor element output data, sensor table data, reference data, and/or other data.

In step 546, the wireless sensor reader 140/340 determines whether any additional specific RF addressable sensors are to be read. If no additional sensors are to be read, operation proceeds to step 560. If additional sensors remain to be read, operation proceeds to step 540.

In step 550, the RFID tag processor 356 isolates an RF addressable sensor 110 from the population 102 using a conventional general read protocol such as binary tree traversal.

In step 552, the wireless sensor reader 140/340 instructs the identified RF addressable sensor 110 to obtain sensor data. This can be done via a predefined command. In an alternate embodiment, RF addressable sensor 110 automatically signals sensor data to wireless sensor reader 140/340. In this embodiment, step 552 is optional.

In step 554, the wireless sensor reader 140/340 receives the sensor data from the RF addressable sensor 110.

In step 556, the wireless sensor reader 140/340 determines whether any additional RF addressable sensors remain to be read. If no additional sensors remain to be read, operation proceeds to step 560. If additional sensors remain to be read, operation proceeds to step 550.

In step 560, the wireless sensor reader 140/340 determines whether any additional processing must be done on the received sensor data. If additional processing must be performed, operation proceeds to step 562. If no additional processing must be performed, operation proceeds to step 570.

In step 562, the wireless sensor reader 140/340 determines whether the additional processing is to be performed locally or remotely. If processing can be performed locally, operation proceeds to step 568. If processing is to be performed remotely, operation proceeds to step 564. For example, some types of processing may be too resource intensive to perform efficiently on the wireless sensor reader 140/340 or may require data not available to the wireless sensor reader 140/340. In this situation, remote sensor processing is selected for the sensor data.

In step 564, the wireless sensor reader 140/340 communicates the received sensor data to sensor network processor 190 over communications network 180. In an embodiment, the wireless sensor reader may also communicate additional data to the sensor network processor 190 such as data needed to perform geolocation. Upon receipt, sensor network processor 190 may perform additional processing on the data and/or perform geolocation to determine the location of the RF addressable sensor 110 that generated the sensor data.

In step 566, wireless sensor reader 140/340 receives the processed sensor data from sensor network processor 190.

In step 568, sensor data processing logic 355 processes the received sensor data.

In step 570, the received sensor data or processed sensor data is displayed. In an embodiment of the present invention, the data is displayed via a user interface 346 on wireless sensor device 140/340. In an alternate embodiment, the data may also be communicated to one or more end user devices over communications network for display. Step 570 is optional.

FIG. 7A is a flowchart of a method 700A for basic RF addressable sensor read communications from the perspective of single RF addressable sensor 110 according to an embodiment of the present invention. Method 700A will be described with continued reference to FIGS. 1 and 2. Note that some steps shown in the flowchart do not necessarily have to occur in the order shown.

Method 700A begins with step 710. In step 710, RF addressable sensor 110 receives RF signals from wireless sensor reader 340. In an embodiment, step 710 includes the step where the received RF signal is used to power sensor 110. Furthermore, step 710 may include the step where sensor 110 identifies itself to reader 340.

In step 720, sensor 110 receives a command from reader 340 to obtain sensor data. Step 720 is optional. In an embodiment of the present invention, RF addressable sensor 110 obtains sensor data automatically each time a communication session with a reader 340 is initiated.

In step 730, analog sensor data is obtained by one or more sensor elements 291, 292 and/or 294 and communicated to ADC 252.

In step 740, ADC converts the analog sensor data into digital sensor data.

In step 780, the RF addressable sensor 110 communicates the digital sensor data to wireless sensor reader 140/340. The details of this communication are dependent upon the protocol used for communication between the wireless sensor reader 140/340 and the RF addressable sensor 110. In an embodiment of the present invention, the protocol used is a binary tree traversal protocol. In this embodiment, the tag identification number signaled by the RF addressable sensor 110 may include both the tag identification number stored in memory 246 and the sensor data obtained by the sensor elements. Alternatively, reader 140/340 may place the RFID tag logic 244 in a command state. In the command state, the RFID tag logic responds to commands received from the reader. When the RFID tag logic 244 receives an obtain sensor data command signal, the RFID tag logic will signal the sensor data to the reader 140/340. In an embodiment, the sensor data communicated to reader 140/340 may include temperature data, sensor data, reference data and/or data stored in sensor data table 258.

FIG. 7B is a flowchart illustrating a method 700B of RF addressable sensor read communications from the perspective of an RF addressable sensor having local processing capabilities, according to an embodiment of the present invention. Method 700B will be described with continued reference to FIGS. 1 and 2. Note that some steps shown in the flowchart do not necessarily have to occur in the order shown.

Steps 710 through 740 are generally the same as steps 710 through 740 discussed above in reference to FIG. 7A.

In step 750, the converted digital sensor data is communicated to sensor processing logic 245.

In step 760, the sensor processing logic 245 processes the converted sensor data.

Step 780 is generally the same as step 780 discussed above in reference to FIG. 7A.

2.2 Example Applications

Homeland Security Sensor Network

The present invention is ideally suited to use for homeland security applications such as the detection of chemical, radiological, or biological agents over large areas, according to an example embodiment of the present invention. An example of this use is presented in the block diagram of FIG. 8 and the associated flowchart of FIG. 9. FIG. 8 depicts a sensor network 800 for monitoring geographical area 820. Sensor network 800 includes a plurality of RF addressable sensors 810a, 810b, and 810c, etc. (collectively sensor elements 810), one or more wireless sensor readers 840, and access points for communications network 880.

One or more of the wireless sensor readers 840 may be a permanent part of the sensor network 800. For example, multiple wireless sensor readers 840 may be affixed to different locations to provide maximum coverage of geographic area 820. In addition, one or more wireless sensor readers 840 may be temporarily part of the sensor network 800. For example, this would be the case when an individual carries a wireless sensor reader 840 capable of reading sensors 810 into geographic area 820. Each wireless sensor reader 840 has a read coverage range 845. Any RF addressable sensor 810 within the read coverage range 845 can be read by the corresponding reader 840.

Any combination of one or more types of sensors can be used in sensor network 800. For example, RF addressable sensors 810a may include sensor elements for detecting chemical agents, sensors 810b include sensor elements for detecting radiological agents, and sensors 810c include sensor elements for detecting biological agents. As would be appreciated by a person skilled in the relevant art(s), other types of sensor elements can be included in this application.

The method 900 depicted in the flowchart of FIG. 9 begins with step 910. In step 910, a plurality of RF addressable sensors 810 are distributed to cover a defined monitoring area. The sensors 810 can be distributed manually or by another means such as scattering by aircraft to cover an even larger geographical area 820.

In step 920, one or more wireless sensor readers 840 initiates a read of sensor elements within its read coverage range 845. For example, a wireless reader 840 may initiate a read of its coverage range every 15 minutes.

In step 930, the wireless sensor reader 840 receives sensor data from the sensor elements within its read coverage range 845.

In step 940, the wireless sensor reader 840 determines whether the sensor data indicates the presence of any dangerous agents. If the data indicates the presence of a dangerous agent, operation proceeds to step 950. If the data indicates that no dangerous agents are present, operation can end, or can proceeds to step 920.

In step 950, the wireless sensor reader 840 performs geolocation processing to determine the exact location of the RF addressable sensor associated with data indicating the presence of a dangerous agent. The geolocation processing could use GPS-based or non-GPS based techniques.

In an alternate embodiment, after performing step 930, the wireless sensor reader 840 communicates the received sensor data to a centralized sensor network processor 890. The sensor network processor 890 then performs steps 940 and 950. In addition, the sensor network processor 890 receives sensor data from all wireless sensor readers 840 in geographic area 820. The sensor network processor 890 then compiles a complete picture of the status of geographic area 820 and can quickly identify and respond to any variations in sensor data from an area within geographic area 820. Cross validation of sensor events is important for network applications, particularly industrial or homeland security applications. For example, individual sensor events will not necessarily yield accurate information and may be, in fact, false positives. However, by matching similar sensor data in a given geographic location at a centralized point, cross validation becomes possible. As a result, the overall data yields greater precision such as the geographical center of the threat, peripheral areas, and areas where the threat is no longer a danger to the public.

Remote Monitoring of Shipping Containers or Cargo

The present invention can also be used for the remote monitoring of shipping containers or any shipping box, according to an example embodiment of the present invention. An example of this use is presented in the block diagram of FIG. 10. Remote shipping container monitoring network 1000 includes one or more shipping packages 1012, one or more shipping containers 1022, at least one transport vessel 1024, a communications network 1080, and a network monitoring processor 1090.

One or more RF addressable sensors 1010 may be affixed to each shipping package 1012 or concealed directly inside the box or crate. The RF addressable sensors 1010 include chemical sensor elements, radiological sensor elements, biological sensor elements or any combination of the above. In an alternate embodiment, a plurality of RF addressable sensors 1010 are affixed to the interior of each shipping container 1022.

Each shipping container 1022 includes at least one wireless sensor reader 1040 for obtaining sensor data from the RF addressable sensors 110. The transport vessel 1024 includes at least one device 1042 capable of receiving communications from a wireless sensor reader 1040. The transport vessel 1024 may also include at least one wireless sensor reader 1040. The device 1042 capable of receiving reader communications is coupled to the communications network. The network monitoring processor 1090 includes logic for receiving sensor data and associated information such as container identification, location, and transport identification. The network monitoring processor 1090 also includes inventory and risk management logic.

In an embodiment of the present invention, the shipping packages 1012 are loaded into one or more shipping containers 1022. The shipping containers are in turn loaded onto a transport vessel 1024. While FIG. 10 depicts the transport vessel as a ship, other types of transport vessels are possible including train, truck, aircraft, or other vehicular transports.

The wireless sensor readers 1040 initiate a read of the RF addressable sensors. For example, a wireless sensor reader 1040 in a shipping container 1022 will initiate a read of the RF addressable sensors stored in the shipping container. In an embodiment, reader 1040 processes received sensor data internally. Additionally or alternatively, wireless sensor reader 1040 will then establish a connection with device 1042. After establishing the connection, wireless sensor reader 1040 communicates the sensor data to the device.

Device 1042 then communicates the data and other associated information (e.g., geolocation) to the network monitoring processor 1090 via the communications network.

Upon receipt of the sensor data and associated information, the network monitoring processor 1090 performs risk assessment processing. This processing identifies the presence of a hazardous chemical, radiological, or biological condition. If a hazardous condition is present, the network monitoring processor 1090 takes appropriate steps to address the condition. The network monitoring processor 1090 may also include a memory for storing received sensor data to create a historical profile for a container and/or transport vessel.

Because RF addressable sensors may be concealed inside shipping boxes, when monitoring for the presence of explosives, because of the low diffusion coefficients for high explosives, proximity factors could make present invention as sensitive or even more sensitive than the most expensive screening technology used in airports.

Specifically the diffusion coefficients for gases in air are relatively low, typically between $6 \times 10^{-6}$ and $1.5 \times 10^{-5}$ m$^2$/sec. If we assume a point source of gas at the origin at r=0, a solution of the following three dimensional diffusion equation yields the concentration, C, as a function of time, t, and of distance, r, from the origin:

$$\partial C/\partial t = D \nabla^2 C$$

where D is the diffusion coefficient.

A solution of this equation is $$C(r,t) = B(\pi D t)^{-3/2} \exp(-r^2/4Dt)$$

The constant B depends on the quantity of gas released at time t=0, and the integral of C(r,t) over all space is independent of time and is just B, the number of molecules released. This solution is simply a Gaussian whose half-width increases in time as $(2Dt)^{1/2}$. Thus, if a one tenth of a mole of gas is released, corresponding to about 2.2 liters at atmospheric pressure or $6 \times 10^{22}$ molecules, then for a diffusion coefficient $D=10^{-5}$ m$^2$/sec the concentration in one hour at 1 m from the source will be 2.5% but at 2 m it will be only 0.023 parts per billion. Thus, there is an advantage in having distributed low cost sensors, even if less sensitive, than relying on centralized units. This analysis applies to still air which would be the case for storage areas, shipping containers, sealed shipping boxes, etc. In open air, turbulence and wind, which may be directional, will overwhelm diffusion. Nevertheless, since the concentration will still rapidly fall off (at least as $1/r^2$ if not exponentially) with distance from the source, the argument that proximity more than makes up for lower sensitivity still holds. Similarly, radiation tags may be concealed directly within the walls of boxes or crates, bringing the sensor very close to the potential source and thereby increasing sensitivity.

Smart Cards and Remote Diagnostics Monitoring

The present invention can also be used for remote diagnostics monitoring, according to an example embodiment of the present invention. An example of this use is presented in the block diagram of FIG. 11. As shown in FIG. 11, remote individual-specific monitoring network 1100 includes one or more smart cards or badges 1103 having at least one RF addressable sensor 1110, a wireless sensor reader 1140, a communications network 1180, and an end user device 1182.

The RF addressable sensor 1110 may have sensor elements for monitoring temperature, chemical composition, biological composition, or a combination of the above for an individual.

The remote monitoring application can have residential, industrial, commercial, security or medical institution applications. In an embodiment of the present invention, smart card or badge 1103 is affixed to a person (or animal) such that the sensor elements of the RF addressable sensor are proximate to the surface of the skin. RF addressable sensor 1110 may include low power sensors to monitor certain conditions or characteristics such as the individual's vital functions. The smart card or badge 1103 is placed within the read range of the wireless sensor reader 1140.

A read of RF addressable sensor 1110 is then activated remotely. For example, in a residential application, a person (e.g., a parent) may connect to the wireless sensor device (e.g., by establishing a phone connection) via an end user device coupled to communications network 1180 to initiate a read. Alternatively, in a medical institution application, a health care provider may connect to the wireless sensor device via a data terminal or telecommunications device. In addition, the medical institution may have a centralized monitoring system 1190 which automatically initiates a read for patients being treated in the medical institution.

Upon initiation of a read, wireless sensor reader 1140 obtains sensor data from RF addressable sensor 1110 and communicates the information to the initiating end user device 1182 or centralized processor 1190. The sensor data is then displayed to the requesting party. Alternatively, centralized processor 1190 may create a historical record of all received sensor data associated with a particular patient or worker. Based on this historical data and any newly received sensor data, the centralized diagnostic processor 1190 can run a variety of algorithms to detect changes in the condition of the patient. The centralized diagnostic processor 1190 can then alert the appropriate personnel when certain changes are detected.

In commercial or industrial settings, the individual-specific monitoring network 1100 can be used to monitor worker exposure to chemicals or environmental conditions. In this embodiment, each worker or a subset of workers has a smart card or badge 1103 containing one or more RF addressable sensors 1110. Sensors 1110 communicate data to reader 1140. This embodiment can further include geolocation processing in the reader or network to determine the location of the smart card or badge 1103 and/or reader 1140.

Remote Monitoring of Refrigerator Contents

The present invention can also be used for the remote monitoring of the contents of an appliance such as a refrigerator, according to an example embodiment of the present invention. An example of this use is presented in the block diagram of FIG. 12. In this application, as shown in FIG. 12, appliance 1201 includes a wireless sensor reader 1240 which is coupled to a communications network 1280.

A user places one or more items into appliance 1201 that have an RF addressable sensor 1210. For example, a product may have an RF addressable sensor 1210 included in the product's packaging. Alternatively, the user may affix an RF addressable sensor 1210 to an item or may immerse or insert an RF addressable sensor into an item (e.g., immersing a sensor into a container of milk).

The user can then remotely initiate a read of the RF addressable sensors 1210 located inside the appliance 1201 via end user device 1282. After the read is completed, the wireless sensor reader 1240 communicates the data to the end user device 1282. The read may include a simple inventory of the contents of the appliance. In an alternate embodiment, the read also include sensor data indicating the freshness of certain food articles.

For example, a person may remotely initiate a read of the contents of their refrigerator to prepare shopping list or identify any food articles which may have spoiled.

Through the RF addressable sensor technology described herein, any appliance can become "smart" and can become connected to any other wireless device such as a cell phone. Further, by combining the present invention with pay-as-you use wireless technology (e.g., prepaid wireless), many types of appliances can be connected to the wireless network because this technology allows for low cost operation and elimination of monthly bills.

Food Testing

The present invention is also ideally suited for food testing applications. FIG. 13A depicts a block diagram of an example real-time food testing application, according to an example embodiment of the present invention. FIG. 13B depicts a block diagram of a network-based food testing application.

In FIG. 13A, a user affixes, immerses, or inserts an RF addressable sensor 1310 onto or into a food item. The RF addressable sensor 1310 includes sensor elements to detect certain chemical compositions. For example, the user may be allergic to peanuts or other food allergen. The user may select an RF addressable sensor 1310 that is capable of detecting the trace presence of peanuts.

The user then initiates a read of the RF addressable sensor 1310 using a wireless sensor reader 1340. The RF addressable sensor 1310 communicates sensor data to the wireless sensor reader 1340 which process the data and displays the data or a message to the user. For example, the reader may display a message indicating that item x (e.g., peanuts) is not present.

FIG. 13B depicts a sensor network 1300 for monitoring food safety. This type of sensor network may be used at a grocery store or a food storage location (e.g., a warehouse). In this application, an RF addressable sensor 1310 is included in the packaging of each food item 1309. For example, each package of meat would include an RF addressable sensor 1310. Sensor network 1300 includes a centralized network processor 1390 for monitoring the safety of the food item. Centralized network processor 1390 has logic to periodically initiate a read of the food items to identify any items that should be removed. Centralized network processor 1390 is coupled to one or more wireless sensor readers 1340 via a communications network.

One or more of wireless sensor readers 1340 may be a permanent part of the network. For example, a supermarket may have one or more wireless sensor readers 1340 covering its meat storage sections and/or storage locations. In addition, one or more wireless sensor readers 1340 may be temporarily part of the network. This would be the case when an individual carries a wireless sensor reader 1340 capable of reading the sensors into the supermarket. This provides an end user with the ability to determine the quality of a food item prior to purchase.

In addition to being able to check the chemical quality of the food items, sensors may be provided that can detect the presence of bacteria such as *E coli* or *Salmonella*.

Drug Interactions

FIG. 14 depicts a block diagram of an example application of a sensor network for identifying potential interactions among prescribed drugs, according to an example embodiment of the present invention. Sensor network 1400 includes one or more drug canisters 1404, a wireless sensor reader 1440, a communications network 1480, and a centralized processor or server 1490. Each drug canister 1404 includes a label 1405 having an RF addressable sensor 1410. The centralized processor 1490 contains a record for each patient indicating drugs currently registered for the patient. In addition, centralized processor 1490 includes a database listing known interaction among drugs.

Using this application, a user (e.g., a pharmacist) initiates a read of RF addressable sensor 1410 attached to canister 1404 for each drug being taken by the user. The attached RF addressable sensor 1410 communicates details related to the drug and prescription such as type, dosage, chemical composition, etc. to the wireless sensor reader 1440. The wireless sensor reader 1440 then communicates these details to the centralized processor 1490. Centralized processor 1490 then registers the drug in the user's record and performs processing to identify any potential interactions with other drugs registered to the user. If a interaction is identified, the centralized processor 1490 communicates the details of the interaction to wireless sensor reader 1440 for display to the user (e.g., pharmacist).

In an alternate embodiment, wireless sensor reader 1440 may have some of the same functionality as centralized processor 1490 to identify potential drug interactions.

Remote Sensing

FIG. 15 depicts a block diagram of an example application of a sensor network 1500 for remote sensing of hazardous conditions, according to an example embodiment of the present invention. In many settings, monitoring for the presence of hazardous conditions is present. However, because of the lethality of hazardous conditions that can occur, human intervention to perform monitoring is not possible. Sensor network 1500 provides the capability for remote access to sensors in order to detect or provide continual monitoring of hazardous conditions.

In this application, RF addressable sensors 1510 are affixed to packages or containers 1509 having contents with potential dangerous attributes (e.g., toxic chemicals). In addition, RF addressable sensors 1510 can be placed throughout the geographic area where packages or containers 1509 having contents with potential dangerous attributes are stored. A wireless sensor reader 1540 can then be introduced into the area. Wireless sensor reader 1540 can be a permanent component of the network (e.g., located in the storage area) or can be temporary (e.g., brought in on a remote controlled device). A user or remote system can then initiate a read of RF addressable sensors 1510 remotely via a communications network 1580. Wireless sensor reader 1540 then obtains the sensor data and communicates the data to the user or remote system. In this way, a person does not have to expose himself or herself to potentially hazardous conditions.

Sensor network 1500 can also be used for remote sensing of non-hazardous conditions. In an embodiment, RF addressable sensor 1510 includes a thermistor. RF addressable sensor 1510 can be remotely interrogated by a low cost wireless reader 1540. For example, RF addressable sensor 1510 can be attached to pipes in a home. A user in a different location can initiate a read of sensor 1510 and obtain temperature data using end-user device 1582. Because the user is accessing the data remotely, the user can check the status of his or her pipes from anywhere in the world. Alternatively, reader 1540 can be programmed to notify the end user device 1582 if a certain pre-set temperature is reached. By combining the present invention with pay-as-you use technology, the costs to provide this type of remote sensor network are reduced.

Shopping

FIG. 16 depicts an example application of a sensor network in retail grocery shopping, according to an example embodiment of the present invention. Shopping network 1600 includes one or more items having RF addressable sensor tags 1610, a wireless sensor reader 1640, a communications network 1680, and a remote network server 1690.

An RF addressable sensor tag 1610 may be placed in the packaging of perishable food items and may also be placed in the packaging of other food items by the manufacturer. In an embodiment, the wireless sensor reader 1640 is located at the checkout station. In an alternate embodiment, a user may have a wireless sensor reader 1640. In another embodiment, reader 1640 may also be integrated into the shopping cart or another device used by a consumer.

When the consumer enters the checkout station, a read of the RF addressable sensors 1610 located in his or her cart is performed. The wireless sensor reader 1640 obtains sensor data and tag identification data and communications this information to server 1690. Server 1690 has logic to determine the ingredients in the product and expiration dates associated with a particular item. The server 1690 communicates the processed results to the wireless sensor reader 1640 for display to the consumer. For example, the reader 1640 may display a warning if any item has expired or has spoiled.

If the consumer is using his or her own wireless sensor reader 1640, the user may store data related to individual-specific allergies or other medical conditions. In this embodiment, the wireless sensor reader 1640 may also display a warning if any item in the cart contains the allergens such as trace peanut products. In addition, the wireless sensor reader 1640 may inventory, calculate, and display the total charge for the items in the cart.

Calibration Sensing

The present invention can also be used in calibration applications. For example, this application is advantageous for persons experiencing allergies and/or certain medical conditions such as asthma. In this application, when a user experiences an allergic reaction or an asthma attack, the user initiates a read of one or more RF addressable sensors in the area. In an embodiment, one or more of the RF addressable sensors may be a component of a smart card or badge. The wireless sensor reader can then record data related to the environment when the condition occurred. The user then repeats this each time the condition is encountered. In this way, the wireless sensor reader accumulates valuable data for the treatment of the condition as well as the future detection of individual-specific chemicals, etc., that may aggravate the condition or cause an attack to occur. For more information on calibration sensing in a conventional sensor network, see U.S. patent application Ser. No. 10/382,606, entitled "Method and Apparatus for Wide Area Surveillance of a Terrorist or Personal Threat," which is incorporated herein by reference in its entirety.

Smart Buildings and Monitoring of Stress

The present invention can also be used for the remote monitoring of stresses in structures such as buildings, according to an example embodiment of the present invention. An example of this use is presented in the block diagram of FIG. 17.

Monitoring network 1700 includes one or more RF addressable sensors 1710 and a wireless sensor reader 1740. Sensors 1710 are utilized within major structures such as buildings to monitor in real time the stress within the structure. In an embodiment, sensors 1710 include a stress sensor element. Sensors 1710 may be placed directly within the structural beams or supports of the building. In an embodiment, RF addressable sensors 1710 may also include motion, radiation, and/or chemical sensor elements for comprehensive remote monitoring of buildings, bridges, homes, tunnels, etc.

One or more wireless readers 1740 may be a permanent dedicated part of network 1700. In addition, one or more wireless readers 1740 may be temporarily part of network 1700.

3. Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A radio frequency (RF) addressable sensor comprising:
   one or more sensor elements;
   a sensor interface having an analog to digital converter coupled to the one or more sensor elements;
   at least one antenna;
   an RF power and communications interface coupled to the at least one antenna and the sensor interface;
   a controller coupled to the RF power and communications interface and the sensor interface; and
   a memory coupled to the controller and the sensor interface, wherein the memory is configured to store a tag identification number;
   wherein the RF addressable sensor communicates with a wireless device that is coupled to a communications network; and
   wherein the wireless device communicates with the RF addressable sensor to obtain sensor data for transmission over the communications network, and
   wherein the RF power and communications interface, memory and sensor interface are implemented in an integrated circuit.

2. The RF addressable sensor of claim 1, wherein the sensor interface further comprises a memory.

3. The RF addressable sensor of claim 2, wherein the memory includes a sensor data table.

4. The RF addressable sensor of claim 3, wherein the sensor data table stores a sensor identification number.

5. The RF addressable sensor of claim 2, wherein the memory is a programmable memory.

6. The RF addressable sensor of claim 1 further comprising one or more reference elements.

7. The RF addressable sensor of claim 1, wherein at least one of the one or more sensor elements are implemented in the integrated circuit.

8. The RF addressable sensor of claim 1 wherein the integrated circuit and the at least one antenna are on a substrate.

9. The RF addressable sensor of claim 8, wherein at least one of the one or more sensor elements is implemented on the substrate.

10. The RF addressable sensor of claim 8, wherein at least one of the one or more sensor elements is external to the substrate.

11. The RF addressable sensor of claim 10, wherein the at least one of the sensor elements external to the substrate is a micro-electrical-mechanical system.

12. The RF addressable sensor of claim 11, wherein the micro-electrical-mechanical system includes a microcantilever device.

13. The RF addressable sensor of claim 10, wherein the at least one of the sensor elements external to the substrate is an accelerometer.

14. The RF addressable sensor of claim 10, wherein the at least one of the sensor elements external to the substrate is an acoustic wave sensor.

15. The RF addressable sensor of claim 10, wherein the at least one of the sensor elements external to the substrate is a piezoelectric sensor.

16. The RF addressable sensor of claim 10, wherein the at least one of the sensor elements external to the substrate is a resistive sensor.

17. The RF addressable sensor of claim 10, wherein the at least one of the sensor elements external to the substrate is a field-effect sensor.

18. The RF addressable sensor of claim 10, wherein the at least one of the sensor elements external to the substrate is a nanosensor.

19. The RF addressable sensor of claim 10, wherein at least one of the sensor elements external to the substrate is coupled to an external power supply.

20. The RF addressable sensor of claim 1 further comprising a thermistor.

21. The RF addressable sensor of claim 1, wherein the RF power and communications interface includes a power generation module that powers the RF addressable sensor.

22. The RF addressable sensor of claim 21, wherein the power generation module includes circuitry for harvesting RF energy.

23. The RF addressable sensor of claim 21, wherein the power generation module includes a power supply.

24. A radio frequency (RF) addressable sensor comprising:
one or more sensor elements;
a sensor interface having an analog to digital converter coupled to the one or more sensor elements;
at least one antenna;
an RF power and communications interface coupled to the at least one antenna and the sensor interface;
a controller coupled to the RF power and communications interface and the sensor interface; and
a memory coupled to the controller and the sensor interface, wherein the memory is configured to store a tag identification number;
wherein the RF addressable sensor communicates with a wireless device that is coupled to a communications network,
wherein the wireless device communicates with the RF addressable sensor to obtain sensor data for transmission over the communications network, and
wherein the sensor interface includes a memory, the memory including a sensor data table,
wherein the sensor data table includes sensor processing information.

25. The RF addressable sensor of claim 24, wherein the sensor processing information includes software for analyzing the sensor data.

26. A radio frequency (RF) addressable sensor comprising:
one or more sensor elements;
a sensor interface having an analog to digital converter coupled to the one or more sensor elements;
at least one antenna;
an RF power and communications interface coupled to the at least one antenna and the sensor interface;
a controller coupled to the RF power and communications interface and the sensor interface; and
a memory coupled to the controller and the sensor interface, wherein the memory is configured to store a tag identification number;
wherein the RF addressable sensor communicates with a wireless device that is coupled to a communications network,
wherein the wireless device communicates with the RF addressable sensor to obtain sensor data for transmission over the communications network, and
wherein the RF addressable sensor is a micro-electrical-mechanical system.

27. The RF addressable sensor of claim 26, wherein at least one of the one or more sensor elements includes a microcantilever device.

28. A radio frequency (RF) addressable sensor comprising:
one or more sensor elements;
a sensor interface having an analog to digital converter coupled to the one or more sensor elements;
at least one antenna;
an RF power and communications interface coupled to the at least one antenna and the sensor interface;
a controller coupled to the RF power and communications interface and the sensor interface; and
a memory coupled to the controller and the sensor interface, wherein the memory is configured to store a tag identification number;
wherein the RF addressable sensor communicates with a wireless device that is coupled to a communications network,
wherein the wireless device communicates with the RF addressable sensor to obtain sensor data for transmission over the communications network, and
wherein at least one of the one or more sensor elements is an antenna.

29. A wireless sensor reader comprising:
at least one antenna configured for communication with one or more radio frequency (RF) addressable sensors;
a controller;
a network communications module coupled to the controller, the network communications module having an interface for coupling to a communications network;
a logic module coupled to the controller; and
a user interface,
wherein the logic module includes a sensor communications module for receiving sensor data from the one or more RF addressable sensors.

30. The wireless sensor reader of claim 29, wherein the communications network is a wireless communications network.

31. The wireless sensor reader of claim 30, wherein the at least one antenna is configured for communication with the communications network.

32. The wireless sensor reader of claim 30, further comprising a network antenna configured for communication with the communications network.

33. The wireless sensor reader of claim 29, wherein the communications network is a public data network.

34. The wireless sensor reader of claim 33, wherein the interface for coupling to the communications network comprises a data communications interface.

35. The wireless sensor reader of claim 29, wherein the user interface includes a preconfigured button for initiating a read of the RF addressable sensors.

36. The wireless sensor reader of claim 29, wherein the RF addressable sensor logic module further comprises:
   a sensor processor having sensor data processing logic; and
   a tag processor.

37. The wireless sensor reader of claim 36, wherein the logic module further comprises a geolocation processor.

38. The wireless sensor reader of claim 37, wherein the geolocation processor comprises logic to perform at least one of GPS-based geolocation and non GPS-based geolocation.

39. The wireless sensor reader of claim 29, further comprising means for receiving sensor processing information over the communications network.

40. The wireless sensor reader of claim 39, wherein the sensor processing information includes software for analyzing sensor data.

41. The wireless sensor reader of claim 29, wherein the controller, network communications module, and user interface are implemented in a wireless communications device.

42. The wireless sensor reader of claim 41, wherein the logic module is implemented in the wireless communications device.

43. The wireless sensor reader of claim 42, wherein the at least one antenna capable of communication with the one or more RF addressable sensors is coupled to the wireless communications device.

44. The wireless sensor reader of claim 42, wherein the wireless communications device includes a programmable processor.

45. The wireless sensor reader of claim 44, wherein the logic module is software stored in the programmable processor.

46. The wireless sensor reader of claim 45, wherein the software is downloaded into the programmable processor over a data interface.

47. The wireless sensor reader of claim 46, wherein the data interface is an infrared interface.

48. The wireless sensor reader of claim 46, wherein the data interface is an air interface.

49. The wireless sensor reader of claim 46, wherein the data interface is an accessory interface.

50. The wireless sensor reader of claim 44, wherein the wireless communications device includes an interface.

51. The wireless sensor reader of claim 50, wherein a second logic module is external to the wireless device.

52. The wireless sensor reader of claim 41, wherein the wireless communications device includes a data interface.

53. The wireless sensor reader of claim 52, wherein the logic module is external to the wireless device and couples to the wireless device via the data interface.

54. The wireless sensor reader of claim 52, wherein the data interface is an infrared interface.

55. The wireless sensor reader of claim 52, wherein the data interface is an accessory interface.

56. The wireless sensor reader of claim 53, wherein the at least one antenna capable of communication with the one or more RF addressable sensors is coupled to the logic module.

57. A RF addressable sensor network, comprising:
   one or more RF addressable sensors;
   one or more wireless sensor readers coupled to a communications network; and
   one or more end user devices coupled to the communications network;
   wherein the one or more wireless sensor readers communicate with the one or more RF addressable sensors to obtain sensor data for transmission over the communications network;
   wherein a wireless sensor reader comprises:
      at least one antenna configured for communication with the one or more radio frequency (RF) addressable sensors,
      a controller,
      a network communications module coupled to the controller, the network communications module having an interface for coupling to a communications network,
      a logic module coupled to the controller, and
      a user interface,
   wherein the logic module includes a sensor communications module for receiving sensor data from the one or more RF addressable sensors.

58. The RF addressable sensor network of claim 57, wherein the communications network includes a wireless communications network and at least one of the one or more wireless sensor readers include a wireless communications device.

59. The RF addressable sensor network of claim 57, wherein the communications network is a data network.

60. The RF addressable sensor network of claim 59, wherein the communications network further comprises a wireless communications network coupled to the data network.

61. The RF addressable sensor network of claim 59, wherein the communications network is the Internet.

62. The RF addressable sensor network of claim 57, further comprising a sensor network processor coupled to the communications network.

63. A RF addressable sensor network, comprising:
   one or more RF addressable sensors;
   one or more wireless sensor readers coupled to a communications network; and
   one or more end user devices coupled to the communications network;
   wherein the one or more wireless sensor readers communicate with the one or more RF addressable sensors to obtain sensor data for transmission over the communications network, and
   a sensor network processor coupled to the communications network, wherein the sensor network processor comprises a geolocation processor and a sensor data processor.

64. The RF addressable sensor network of claim 63 wherein the geolocation processor includes logic to perform GPS based geolocation and non-GPS based geolocation.

65. A method in a wireless sensor reader for obtaining sensor data from one or more radio frequency (RF) addressable sensors and for communicating the sensor data over a communications network, comprising:
   (a) transmitting signals to the one or more RF addressable sensors wherein the signals initialize the one or more RF addressable sensors;
   (b) interrogating the one or more RF addressable sensors to isolate an individual RF addressable sensor;
   (c) receiving sensor data from the isolated RF addressable sensor;
   (d) determining whether processing of the received sensor data is required;
   (e) if it is determined in step (d) that no processing of the received sensor data is required, displaying the sensor data at the wireless sensor reader;

(f) if it is determined in step (d) that processing of the received sensor data is required, determining whether processing is to be performed at the wireless sensor reader;

(g) if it is determined in step (f) that processing of the received sensor data is to be performed at the wireless sensor reader, performing the steps of:
processing the received sensor data, and
displaying the processed sensor data at the wireless sensor reader; and (h) if it is determined in step (f) that processing of the received sensor data is not to be performed at the wireless sensor reader, performing the steps of:
communicating the received sensor data over the communications network to a network sensor processor,
receiving processed sensor data, and
displaying the processed sensor data at the wireless sensor reader.

66. The method of claim 65, further comprising:
prior to step (a), performing the steps of:
receiving a connection signal from an end user device coupled to the communications network;
connecting to the end user device over the communications network; and
receiving one or more initiation signals from the end user device.

67. The method of claim 65, wherein interrogating the one or more RF addressable sensors includes automatically interrogating the one or more RF addressable sensors on occurrence of an event.

68. The method of claim 67, wherein the event is the passage of a predefined period of time.

69. The method of claim 65, wherein the wireless sensor reader includes a user interface having a keypad and a display.

70. The method of claim 69, wherein interrogating the one or more RF addressable sensors comprises entering a sequence of key strokes via the keypad.

71. The method of claim 69, wherein interrogating the one or more RF addressable sensors comprises activating an item on the display.

72. The method of claim 65, wherein the wireless sensor reader includes a button preconfigured to interrogate the one or more RF addressable sensors.

73. The method of claim 72, wherein interrogating the one or more RF addressable sensors comprises pressing the preconfigured button.

74. The method of claim 65, further comprising:
prior to step (a),
receiving one or more initiation signals from an RF addressable sensor.

75. The method of claim 65, further comprising:
prior to step (a),
receiving logic for obtaining sensor data from the one or more RF addressable sensors.

76. A method in a radio frequency (RF) addressable sensor for communicating sensor data to a wireless sensor reader for transmission over a communications network, wherein the RF addressable sensor includes one or more sensor elements, comprising:
(a) receiving signals from the wireless sensor reader;
(b) obtaining analog sensor data from at least one sensor element;
(c) converting the analog sensor data to digital sensor data;
(d) communicating the digital sensor data to the wireless sensor reader for transmission over the communications network; and
(e) communicating a stored tag identification number to the wireless sensor reader;
wherein communicating the digital sensor data to the wireless sensor reader includes communicating the digital sensor data as a component of the tag identification number.

77. The method of claim 76, further comprising prior to step (b) receiving a read sensor signal from the wireless sensor reader.

78. The method of claim 76, further comprising prior to step (d) processing the digital sensor data.

79. A method in a radio frequency (RF) addressable sensor for communicating sensor data to a wireless sensor reader for transmission over a communications network, wherein the RF addressable sensor includes one or more sensor elements, comprising:
(a) receiving signals from the wireless sensor reader;
(b) obtaining analog sensor data from at least one sensor element;
(c) converting the analog sensor data to digital sensor data;
(d) communicating the digital sensor data to the wireless sensor reader for transmission over the communications network; and
(e) communicating reference data to the wireless sensor reader.

80. A method in a radio frequency (RF) addressable sensor for communicating sensor data to a wireless sensor reader for transmission over a communications network, wherein the RF addressable sensor includes one or more sensor elements, comprising:
(a) receiving signals from the wireless sensor reader;
(b) obtaining analog sensor data from at least one sensor element;
(c) converting the analog sensor data to digital sensor data;
(d) communicating the digital sensor data to the wireless sensor reader for transmission over the communications network; and
(e) communicating sensor processing information to the wireless sensor reader.

81. A method in a wireless sensor reader for obtaining sensor data from one or more radio frequency (RF) addressable sensors, comprising:
transmitting signals to the one or more RF addressable sensors wherein the signals initialize the one or more RF addressable sensors;
interrogating the one or more RF addressable sensors to isolate an individual RF addressable sensor;
receiving sensor data from the isolated RF addressable sensor, wherein the received sensor data includes sensor identification information;
communicating sensor identification information to a processor external to the wireless sensor reader;
receiving sensor data processing information; and
processing the sensor data based on the received processing information.

82. The method of claim 81 wherein the received sensor data processing information includes software for analyzing the received sensor data.

83. A method in a wireless sensor reader for obtaining sensor data from one or more radio frequency (RF) addressable sensors, comprising:
transmitting signals to the one or more RF addressable sensors, wherein the signals initialize the one or more RF addressable sensors;
interrogating the one or more RF addressable sensors to isolate an individual RF addressable sensor;

receiving sensor data from the isolated RF addressable sensor, wherein the received sensor data includes sensor processing information; and processing the sensor data based on the received processing information.

84. The method of claim 83 wherein the received sensor processing information includes software for analyzing the received sensor data.

85. A radio frequency (RF) addressable sensor comprising:

one or more sensor elements;

a sensor interface having an analog to digital converter coupled to the one or more sensor elements;

at least one antenna;

an RF power and communications interface coupled to the at least one antenna and the sensor interface;

a controller coupled to the RF power and communications interface and the sensor interface; and a memory coupled to the controller and the sensor interface, wherein the memory is configured to store a tag identification number;

wherein the sensor interface includes a memory, the memory including a sensor data table, wherein the RF power and communications interface, memory and sensor interface are implemented in an integrated circuit.

* * * * *

UNITED STATES PATENT AND TRADEMARK OFFICE
CERTIFICATE OF CORRECTION

PATENT NO. : 7,148,803 B2  Page 1 of 1
APPLICATION NO. : 10/761362
DATED : December 12, 2006
INVENTOR(S) : Bandy et al.

It is certified that error appears in the above-identified patent and that said Letters Patent is hereby corrected as shown below:

On Title Page 2, in Field (56), under "OTHER PUBLICATIONS", in Column 2, Line 7, delete "al," and insert -- al., --, therefor.

On Title Page 2, in Field (56), under "OTHER PUBLICATIONS", in Column 2, Line 10, delete "Arneson et al, entitled" and insert -- entitled --, therefor.

In Fig. 5, Sheet 5 of 16, for Tag "544", in Line 1, delete "RECIEVE" and insert -- RECEIVE --, therefor.

In Fig. 5, Sheet 5 of 16, for Tag "554", in Line 1, delete "RECIEVE" and insert -- RECEIVE --, therefor.

In Fig. 15, Sheet 15 of 16, for Tag "1580", in Line 1, delete "PUBLICY" and insert -- PUBLICLY --, therefor.

In Column 10, Line 51, delete "sensor" and insert -- sensor. --, therefor.

In Column 19, Line 38, delete "6×10$^{22}$molecules," and insert -- 6×10$^{22}$ molecules, --, therefor.

In Column 24, Line 59, in Claim 8, delete "claim 1" and insert -- claim 1, --, therefor.

Signed and Sealed this
Seventh Day of August, 2012

David J. Kappos
*Director of the United States Patent and Trademark Office*

(12) INTER PARTES REEXAMINATION CERTIFICATE (0205th)
United States Patent
Bandy et al.

(10) Number: US 7,148,803 C1
(45) Certificate Issued: Nov. 9, 2010

(54) RADIO FREQUENCY IDENTIFICATION (RFID) BASED SENSOR NETWORKS

(75) Inventors: William R. Bandy, Gambrills, MD (US); John P. Peeters, Chincoteague, VA (US)

(73) Assignee: Symbol Technologies, Inc., Holtsville, NY (US)

Reexamination Request:
No. 95/001,014, Nov. 6, 2007

Reexamination Certificate for:
Patent No.: 7,148,803
Issued: Dec. 12, 2006
Appl. No.: 10/761,362
Filed: Jan. 22, 2004

Related U.S. Application Data

(60) Provisional application No. 60/513,740, filed on Oct. 24, 2003.

(51) Int. Cl.
*G08B 1/08* (2006.01)

(52) U.S. Cl. ............... 340/539.16; 340/10.1; 340/505; 340/539.17; 340/539.22; 340/539.26; 340/870.11; 340/870.16

(58) Field of Classification Search .................... None
See application file for complete search history.

(56) References Cited

U.S. PATENT DOCUMENTS

| | | | |
|---|---|---|---|
| 5,347,274 A | 9/1994 | Hassett | |
| 5,856,788 A | 1/1999 | Walters et al. | |
| 5,862,803 A | 1/1999 | Besson et al. | |
| 5,917,433 A | 6/1999 | Keillor et al. | |
| 6,259,373 B1 | 7/2001 | Ghahramani | |
| 6,437,692 B1 | 8/2002 | Petite et al. | |
| 6,720,628 B2 | 4/2004 | Karasawa et al. | |
| 6,917,291 B2 | 7/2005 | Allen | |
| 7,035,818 B1 | 4/2006 | Bandy et al. | |
| 2003/0017804 A1 | 1/2003 | Heinrich | |
| 2004/0069850 A1 | 4/2004 | De Wilde | |
| 2004/0100394 A1 | 5/2004 | Hitt | |
| 2004/0113790 A1 | 6/2004 | Hamel et al. | |
| 2005/0087235 A1 | 4/2005 | Skorpik et al. | |
| 2006/0164239 A1 | 7/2006 | Loda | |
| 2006/0181414 A1 | 8/2006 | Bandy et al. | |

FOREIGN PATENT DOCUMENTS

| | | |
|---|---|---|
| GB | 2 308 947 A | 7/1997 |
| WO | 03/098175 A1 | 11/2003 |

OTHER PUBLICATIONS

Microelectromechanical systems (from Wikipedia encyclopedia, Dec. 15, 2008).*
Computer software (from Wikipedia encyclopedia, Dec. 17, 2008).*
Telecommunication network (from Wikipedia encyclopedia, Dec. 16, 2008).*

* cited by examiner

*Primary Examiner*—Anjan K. Deb

(57) ABSTRACT

An RF addressable sensor network architecture is provided. The RF addressable sensor network includes one or more RF addressable sensors, one or more wireless sensor readers coupled to a communications network, and one or more end user devices coupled to the communications network. The RF addressable sensor network may also include a sensor network processor. An RF addressable sensor includes one or more sensor elements, one or more antennas for communicating with the wireless sensor reader, an RF power and communications interface, an RFID control module, and a sensor interface. The wireless sensor reader includes one or more antennas, a user interface, a controller, a network communications module, and an RF addressable sensor logic module.

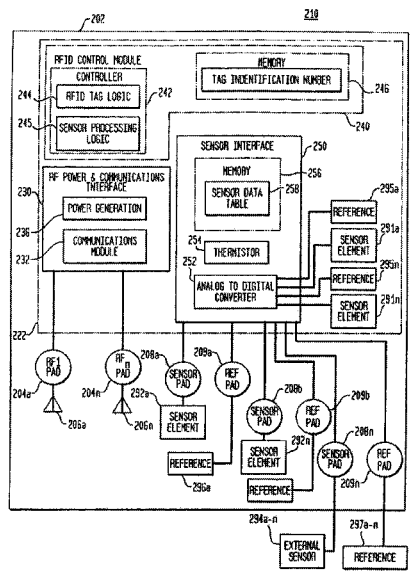

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 11, 12, 26 and 27 is confirmed.

Claims 1-10, 13-25 and 28-85 are cancelled.

\* \* \* \* \*